United States Patent
Aoyama

(10) Patent No.: US 11,439,297 B2
(45) Date of Patent: Sep. 13, 2022

(54) MEDICAL IMAGE PROCESSING SYSTEM, ENDOSCOPE SYSTEM, DIAGNOSIS SUPPORT APPARATUS, AND MEDICAL SERVICE SUPPORT APPARATUS

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 224 days.

(21) Appl. No.: 16/824,629

(22) Filed: Mar. 19, 2020

(65) Prior Publication Data
US 2020/0214547 A1 Jul. 9, 2020

Related U.S. Application Data

(63) Continuation of application No. PCT/JP2018/033756, filed on Sep. 12, 2018.

(30) Foreign Application Priority Data

Sep. 22, 2017 (JP) .............................. JP2017-181906

(51) Int. Cl.
*A61B 1/00* (2006.01)
*A61B 1/06* (2006.01)
(Continued)

(52) U.S. Cl.
CPC ........ *A61B 1/0684* (2013.01); *A61B 1/00188* (2013.01); *A61B 1/045* (2013.01);
(Continued)

(58) Field of Classification Search
CPC ... A61B 1/0684; A61B 1/00188; A61B 1/045; A61B 1/05; A61B 1/0638;
(Continued)

(56) References Cited

U.S. PATENT DOCUMENTS 9,095,269 B2 *  8/2015  Morita .................... A61B 1/05
9,826,894 B2   11/2017  Masaki et al.
(Continued)

FOREIGN PATENT DOCUMENTS

CN    105407789    3/2016
CN    106793932    5/2017
(Continued)

OTHER PUBLICATIONS

"International Search Report (Form PCT/ISA/210) of PCT/JP2018/033756," dated Nov. 13, 2018, with English translation thereof, pp. 1-3.
(Continued)

*Primary Examiner* — Timothy J Neal
*Assistant Examiner* — Sung Ham
(74) *Attorney, Agent, or Firm* — JCIPRNET

(57) ABSTRACT

An imaging unit acquires a white light image by imaging an observation target being illuminated with white light, and acquires a specific light image by imaging the observation target being illuminated with specific light. A light source control unit controls the number of light emission frames of the white light and the number of light emission frames of the specific light in one light emission cycle according to at least one of a moving speed of the imaging unit, zoom information, or a light emission amount.

15 Claims, 13 Drawing Sheets

(51) Int. Cl.
  *A61B 1/045* (2006.01)
  *A61B 1/05* (2006.01)
  *A61B 90/30* (2016.01)
  *A61B 1/005* (2006.01)

(52) U.S. Cl.
  CPC .............. *A61B 1/05* (2013.01); *A61B 1/0638* (2013.01); *A61B 1/00045* (2013.01); *A61B 1/0051* (2013.01); *A61B 2090/309* (2016.02)

(58) Field of Classification Search
  CPC .............. A61B 1/00045; A61B 1/0051; A61B 2090/309; A61B 1/0646; A61B 1/00009; A61B 1/00055; A61B 1/00006; G06T 7/0014; G06T 7/0016; G06T 11/003; G06T 2207/30004; G06T 2207/30168; G06T 2207/10068; G06T 2207/10152; G06T 2207/30101; G06T 7/0012; H04N 2005/2255
  USPC ........ 382/128, 129, 130, 131, 132, 133, 134
  See application file for complete search history.

(56) References Cited

U.S. PATENT DOCUMENTS

| | | | |
|---|---|---|---|
| 10,531,008 B2 | 1/2020 | Yabe et al. | |
| 10,610,083 B2 | 4/2020 | Nishio et al. | |
| 2010/0063352 A1* | 3/2010 | Matsuura | H04N 5/23293 600/103 |
| 2012/0016230 A1 | 1/2012 | Kishima et al. | |
| 2012/0271103 A1 | 10/2012 | Gono et al. | |
| 2012/0327205 A1 | 12/2012 | Takahashi | |
| 2014/0316279 A1* | 10/2014 | Morishita | A61B 1/0638 600/476 |
| 2015/0181185 A1* | 6/2015 | Ikemoto | A61B 1/0684 348/71 |
| 2016/0089012 A1* | 3/2016 | Aoyama | A61B 1/0638 348/71 |
| 2017/0112356 A1* | 4/2017 | Mitsui | A61B 1/0646 |
| 2017/0135555 A1 | 5/2017 | Yoshizaki | |
| 2017/0251932 A1* | 9/2017 | Kaku | A61B 1/00009 |
| 2017/0280971 A1* | 10/2017 | Makino | G06T 7/0012 |
| 2018/0064319 A1* | 3/2018 | Hayashi | A61B 1/045 |
| 2020/0146529 A1* | 5/2020 | Kono | G06K 9/628 |

FOREIGN PATENT DOCUMENTS

| | | |
|---|---|---|
| CN | 107072518 | 8/2017 |
| EP | 2022388 | 2/2009 |
| JP | 2011135983 | 7/2011 |
| JP | 2015054062 | 3/2015 |
| JP | 2016192986 | 11/2016 |
| WO | 2017085793 | 5/2017 |

OTHER PUBLICATIONS

"Written Opinion of the International Searching Authority (Form PCT/ISA/237) of PCT/JP2018/033756," dated Nov. 13, 2018, with English translation thereof, pp. 1-16.

"Search Report of Europe Counterpart Application", dated Sep. 8, 2020, p. 1-p. 6.

Office Action of Japan Counterpart Application, with English translation thereof, dated Mar. 23, 2021, pp. 1-7.

Office Action of China Counterpart Application, with English translation thereof, dated Nov. 3, 2021, pp. 1-15.

* cited by examiner

MEDICAL IMAGE PROCESSING SYSTEM, ENDOSCOPE SYSTEM, DIAGNOSIS SUPPORT APPARATUS, AND MEDICAL SERVICE SUPPORT APPARATUS

CROSS-REFERENCE TO RELATED APPLICATIONS

This application is a Continuation of PCT International Application No. PCT/JP2018/033756 filed on 12 Sep. 2018, which claims priority under 35 U.S.C. § 119(a) to Japanese Patent Application No. 2017-181906 filed on 22 Sep. 2017. The above application is hereby expressly incorporated by reference, in its entirety, into the present application.

BACKGROUND OF THE INVENTION

1. Field of the Invention

The present invention relates to a medical image processing system, an endoscope system, a diagnosis support apparatus, and a medical service support apparatus which use white light for observing an observation target and specific light for detecting a region of interest such as a lesion area.

2. Description of the Related Art

In the current medical field, medical image processing systems using medical images are widespread in diagnosis of an observation target. Among the medical image processing systems, an endoscope system acquires an endoscopic image that is one of medical images by irradiating an observation target with illumination light and imaging the observation target. The acquired endoscopic image is displayed on a display unit such as a monitor, and is used in diagnosis of the observation target.

In the endoscope system in recent years, it is easy to detect a lesion area by illuminating an observation target with specific light having a specific wavelength range including shortwave narrow-band light to improve visibility of the lesion area on the observation target. However, since a specific light image obtained using specific light is displayed in a color different from a color of the observation target, such as a pseudo color, a user may not be familiar with the specific light image as compared with a white light image used in normal observation, in many cases. Thus, in JP2011-135983A (corresponding to US2012/327205A1), a lesion region is detected from a specific light image and the detected lesion region is highlighted in a white light image so that the lesion region can be observed on the white light image which is familiar.

SUMMARY OF THE INVENTION

In the endoscope observation, an observation situation for the observation target is changed depending on operation aspects by a user, diagnosis purposes, and the like. For example, the moving speed of the endoscope is increased in a region where there is no lesion area, or a region where confirmation of the lesion is easy, whereas the moving speed of the endoscope is decreased in a region suspected to be a lesion area or a region where confirmation of the lesion is difficult. In a case where a lesion area is detected or the like, the region that seems to be a lesion is enlarged by using zooming of the endoscope. Further, observation is performed with low light intensity in a case where the endoscope is far from the observation target as in screening, whereas observation is performed with high light intensity in a case where the endoscope is close to the observation target as in case of discriminating a lesion area.

Here, in a case where the lesion region detected from the specific light image based on the specific light is observed on the white light image as in JP2011-135983A, when the observation situation such as the moving speed of the endoscope, using or non-using of zooming, and light intensity is changed, the lesion area may not be detected from the specific light image, and thus it becomes difficult to grasp the observation target on the white light image.

For example, in a case of illuminating the observation target by switching between white light and specific light, the frame rate of white light is dropped resulting in the observation image that seems to have dropped frames. In a case where a CMOS image sensor is used to image the observation target, the decrease in frame rate becomes significant due to a rolling shutter. Further, in a case where a ratio of light emission frames of the specific light is decreased in order to suppress the frame drop of the observation image, the timing at which the lesion area can be detected is reduced, and thus the lesion area may be overlooked. In particular, in the endoscope, since the appearance is changed by a subtle difference in imaging angle or distance even at the same location, a possibility that the lesion area is overlooked is increased by reducing the ratio of the light emission frames of the specific light.

An object of the invention is to provide a medical image processing system, an endoscope system, a diagnosis support apparatus, and a medical service support apparatus which can reliably detect a region of interest such as a lesion area and make it easy to grasp an observation target in accordance with an observation situation which is changed depending on an operation aspect by a user or a diagnosis purpose.

A medical image processing system according to an aspect of the invention comprises a light source unit, an imaging unit, an observation situation acquisition unit, and a light source control unit. The light source unit emits white light or specific light having a spectrum different from a spectrum of the white light. The imaging unit acquires a white light image by imaging an observation target being illuminated with the white light, and acquires a specific light image by imaging the observation target being illuminated with the specific light. The observation situation acquisition unit acquires at least one of a moving speed of the imaging unit, zoom information relating to zooming of enlarging the observation target, or a light emission amount of the white light or the specific light. The light source control unit controls the number of light emission frames of the white light and the number of light emission frames of the specific light in one light emission cycle according to the at least one of the moving speed of the imaging unit, the zoom information, or the light emission amount of the white light or the specific light. Further, it is preferable that the medical image processing system further comprises a region-of-interest detection unit that performs region-of-interest detection processing for detecting a region of interest from the specific light image, and a display unit that displays a region-of-interest display image obtained by reflecting a detection result of the region-of-interest detection unit in the white light image.

It is preferable that the light source control unit performs control such that the number of light emission frames of the specific light is greater than the number of light emission frames of the white light at a time of using the zooming, and may perform control such that the number of light emission frames of the white light is greater than the number of light emission frames of the specific light at a time of not using the zooming. It is preferable that the light source control unit performs control such that the number of light emission frames of the white light is greater than the number of light emission frames of the specific light in a case where the moving speed of the imaging unit exceeds a speed threshold, and may perform control such that the number of light emission frames of the specific light is greater than the number of light emission frames of the white light in a case where the moving speed of the imaging unit is equal to or less than the speed threshold. It is preferable that the light source control unit performs control such that the number of light emission frames of the white light is greater than the number of light emission frames of the specific light in a case where the light emission amount of the white light or the specific light exceeds a light emission amount threshold, and may perform control such that the number of light emission frames of the specific light is greater than the number of light emission frames of the white light in a case where the light emission amount of the white light or the specific light is equal to or less than the light emission amount threshold.

It is preferable that the medical image processing system further includes a specific light detection result decision unit which, in a case where a plurality of the specific light images are obtained from a plurality of light emission frames of the specific light and the region-of-interest detection processing is performed on the specific light images, decides a specific light detection result to be reflected in the white light image on the basis of a detection result of the region-of-interest detection processing on the specific light images. It is preferable that in a case where both results with the detection of the region of interest and results without the detection of the region of interest are obtained for the same region of the observation target from the plurality of specific light images, the specific light detection result decision unit decides, as the specific light detection result, any of the results with the detection of the region of interest or the results without the detection of the region of interest by a majority based on the number of results with the detection of the region of interest and the number of results without the detection of the region of interest.

It is preferable that the medical image processing system further includes a discrimination unit that performs discrimination processing for discriminating the observation target included in the region of interest, and a result of the discrimination processing is displayed on the display unit. It is preferable that the medical image processing system further includes a discrimination result decision unit which, in a case where a plurality of the specific light images are obtained from a plurality of light emission frames of the specific light, the region-of-interest detection processing is performed on the specific light images, and the discrimination processing is performed on the regions of interest detected in the region-of-interest detection processing, decides a specific light discrimination result to be displayed on the display unit on the basis of a result of the discrimination processing on the regions of interest.

It is preferable that the result of the discrimination processing is expressed by a stage decided according to a state of the observation target, and the discrimination result decision unit, in a case where a plurality of results of the discrimination processing with different stages are obtained for the same region of interest, decides the stage as the specific light discrimination result by a majority based on the plurality of results of the discrimination processing. It is preferable that the result of the discrimination processing is expressed by a stage decided according to a state of the observation target, and the discrimination result decision unit, in a case where a plurality of results of the discrimination processing with different stages are obtained for the same region of interest, decides the stage as the specific light discrimination result by averaging the plurality of results of the discrimination processing.

It is preferable that in a case where the discrimination processing is performed, the light source unit emits illumination light for discrimination instead of or in addition to the specific light. It is preferable that 410 nm is included in a peak wavelength of the illumination light for discrimination. It is preferable that 450 nm is included in a peak wavelength of the specific light.

An endoscope system according to an aspect of the invention comprises a light source unit, an endoscope, an observation situation acquisition unit, and a light source control unit. The light source unit emits white light or specific light having a spectrum different from a spectrum of the white light. The endoscope includes an imaging unit that acquires a white light image by imaging an observation target being illuminated with the white light, and acquires a specific light image by imaging the observation target being illuminated with the specific light. The observation situation acquisition unit acquires an observation situation including at least one of a moving speed of the endoscope, zoom information relating to zooming of enlarging the observation target, or a light emission amount of the white light or the specific light. The light source control unit controls a ratio of light emission frames of the white light and light emission frames of the specific light according to the at least one of the moving speed of the endoscope, the zoom information, or the light emission amount of the white light or the specific light. Further, it is preferable that the medical image processing system further comprises a region-of-interest detection unit that performs region-of-interest detection processing for detecting a region of interest from the specific light image, and a display unit that displays a region-of-interest display image obtained by reflecting a detection result of the region-of-interest detection unit in the white light image.

A diagnosis support apparatus according to an aspect of the invention includes the above-described medical image processing system according to an aspect of the invention. A medical service support apparatus according to an aspect of the invention includes the above-described medical image processing system according to an aspect of the invention.

According to the invention, it is possible to reliably detect a region of interest such as a lesion area and make it easy to grasp an observation target in accordance with an observation situation which is changed depending on an operation aspect by a user or a diagnosis purpose.

DESCRIPTION OF THE PREFERRED EMBODIMENTS

First Embodiment

Figure 1:
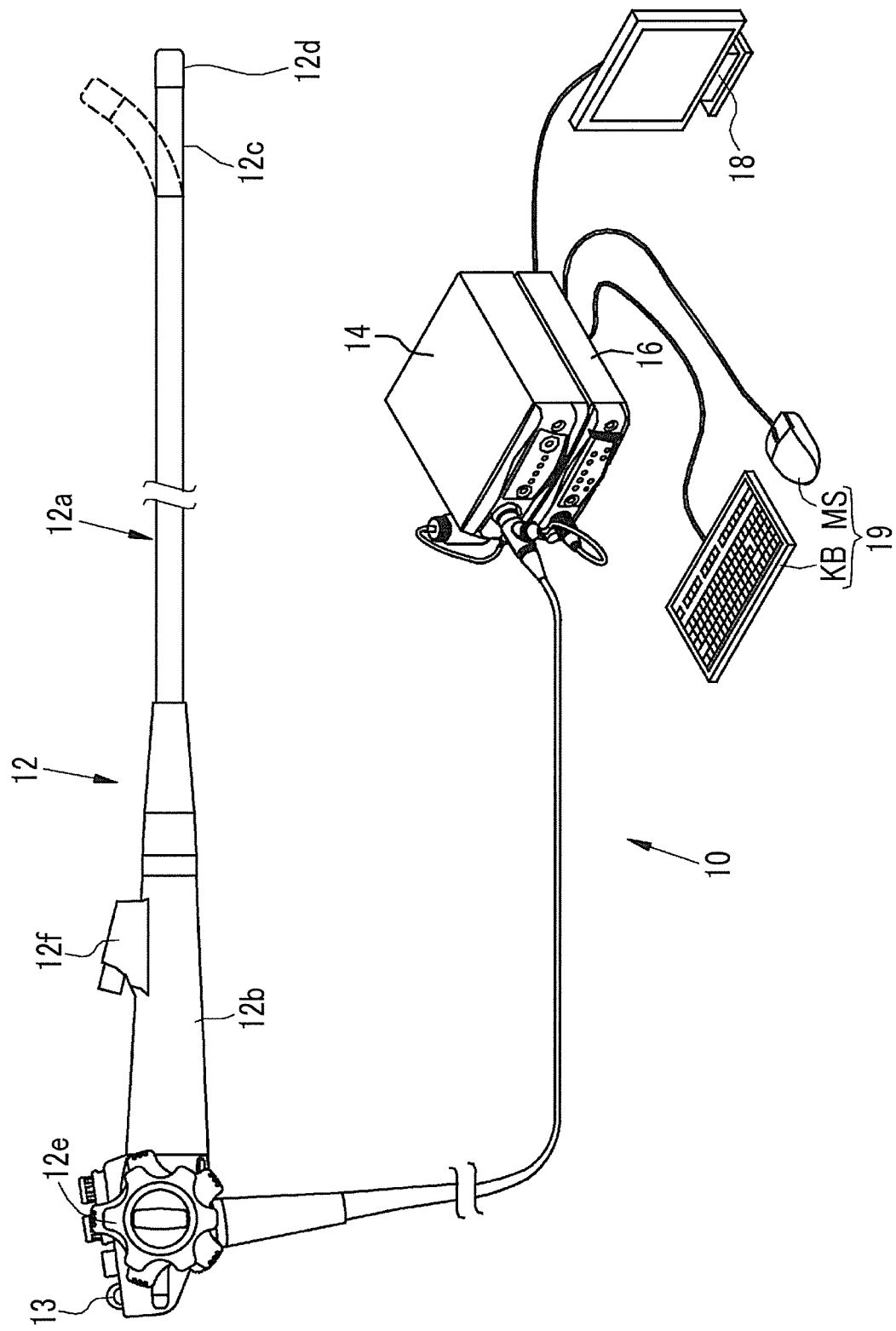
FIG. 1 is an external view of an endoscope system.

As shown in FIG. 1, an endoscope system 10 comprises an endoscope 12, a light source device 14, a processor device 16, a monitor 18, and a user interface 19. The endoscope 12 irradiates an observation target with illumination light, and images the observation target irradiated with the illumination light. The light source device 14 generates illumination light to be emitted to the observation target. The processor device 16 performs system control of the endoscope system 10, image processing, and the like. The monitor 18 is a display unit that displays an image output from the processor device 16. The user interface 19 is an input device for performing a setting input or the like with respect to the processor device 16 and the like, and is configured to include a keyboard KB, a mouse MS, and the like.

The endoscope 12 has an insertion part 12a that is to be inserted into a subject, an operation part 12b provided in a proximal end portion of the insertion part 12a, and a bendable portion 12c and a distal end portion 12d that are provided on the distal end side of the insertion part 12a. The bendable portion 12c is bent by operating an angle knob 12e of the operation part 12b. The distal end portion 12d is directed in a desired direction by the bending of the bendable portion 12c. A spray port (not shown) for spraying air, water, or the like toward the observation target is provided in the distal end portion 12d.

In addition to the angle knob 12e, a zoom operation part 13 is provided in the operation part 12b. The observation target can be imaged in an enlarged or reduced manner by operating the zoom operation part 13. A forceps channel (not shown) for inserting a treatment tool and the like is provided from the insertion part 12a to the distal end portion 12d. The treatment tool is inserted into the forceps channel from a forceps inlet 12f.

Figure 2:
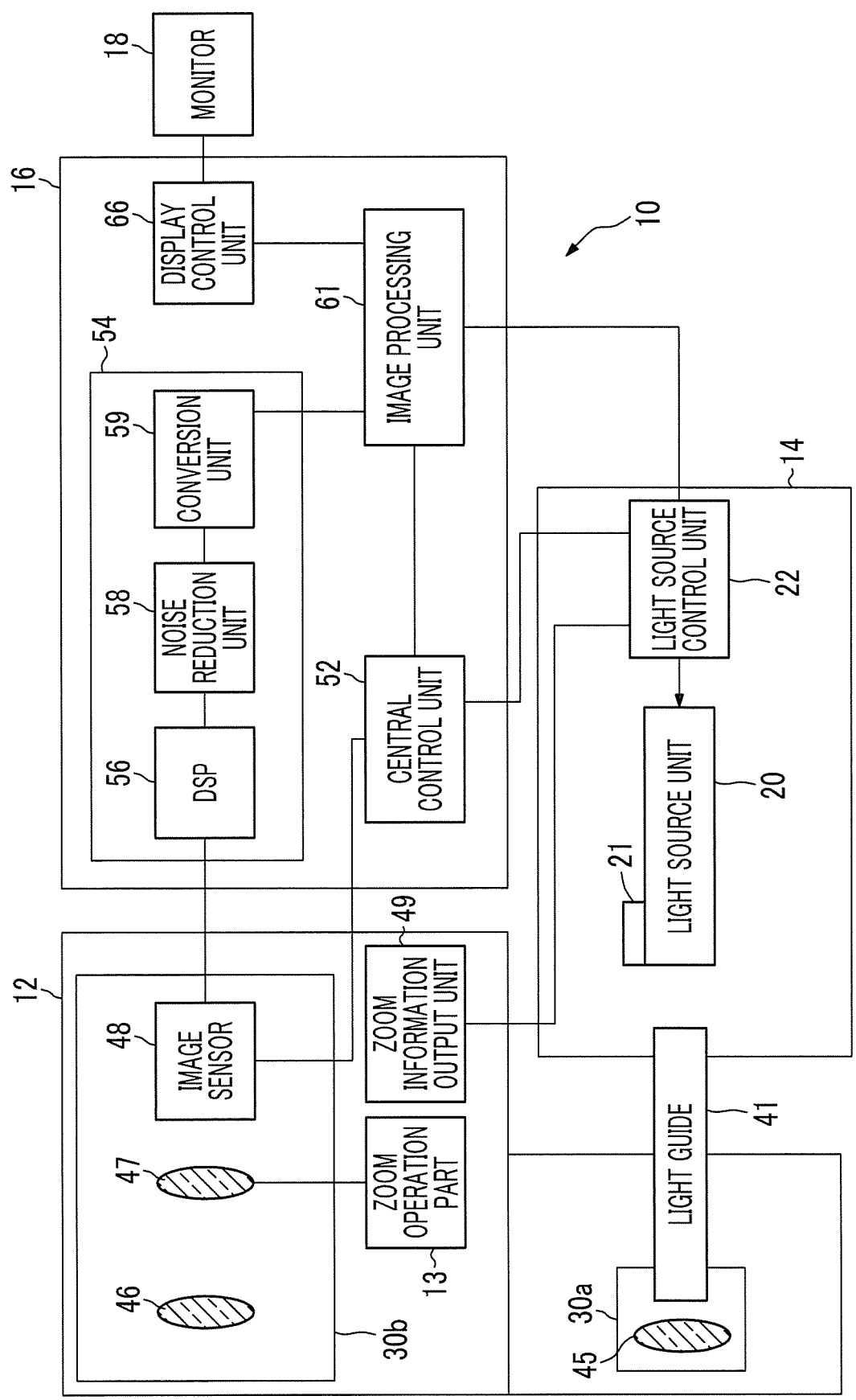
FIG. 2 is a block diagram of the endoscope system.

As shown in FIG. 2, the light source device 14 comprises a light source unit 20 and a light source control unit 22. The light source unit 20 emits illumination light for illuminating the observation target. The light source unit 20 comprises one or a plurality of light sources, and emits a plurality of rays of illumination light including white light or specific light having a spectrum different from that of white light. Specifically, the light source unit 20 emits white light having a blue-light wavelength range, a green-light wavelength range, and a red-light wavelength range or specific light having a specific wavelength range where 450 nm is included in the peak wavelength. A light emission amount measurement unit 21 which measures a light emission amount of white light or a light emission amount of specific light is provided to the light source unit 20. Information regarding the light emission amount of white light or the light emission amount of specific light is transmitted to the light source control unit 22. An "observation situation acquisition unit" of the invention corresponds to the "light emission amount measurement unit 21".

The light source control unit 22 controls the driving of the light source unit 20. The light source control unit 22 independently controls the timing of turning on or off the light sources constituting the light source unit 20, and the light emission amount or the like at the time of lighting. As a result, the light source unit 20 can emit a plurality of kinds of rays of illumination light with different light emission amounts and different light emission timings. In the light source device 14, as light emission modes for controlling the light emission of the light source unit 20, there are a normal mode in which white light is emitted, and a special mode in which white light and specific light are automatically switched and emitted according to a specific light emission pattern.

In a case where the special mode is set, the light source control unit 22 sets a specific light emission pattern according to the moving speed of the endoscope 12, zoom information, or the light emission amount of white light or specific light. For example, in a case where the moving speed of the endoscope 12 exceeds a speed threshold, the light source control unit 22 sets, as the specific light emission pattern, a first light emission pattern in which the number of light emission frames of white light is greater than the number of light emission frames of specific light in one light emission cycle, and performs light emission control on the basis of the first light emission pattern. Here, the one light emission cycle consists of a specific number of light emission frames, and includes a light emission frame for emitting white light and a light emission frame for emitting specific light.

In this manner, in a case where the moving speed of the endoscope 12 exceeds the speed threshold, since it is considered that the necessity for detecting a lesion area is low under a situation where a region with no lesion or a region where confirmation of a lesion is easy is observed, the first light emission pattern in which the number of light emission frames of specific light is low is set. The number of light emission frames (sum of the number of light emission frames of white light and the number of light emission frames of specific light) per one light emission cycle may be fixed, or may be changed according to a specific frame number change condition. For example, in a case where the number of light emission frames per one light emission cycle is 9, the number of light emission frames per one light emission frame is changed to 5 when the specific frame number change condition is satisfied.

Figure 3:
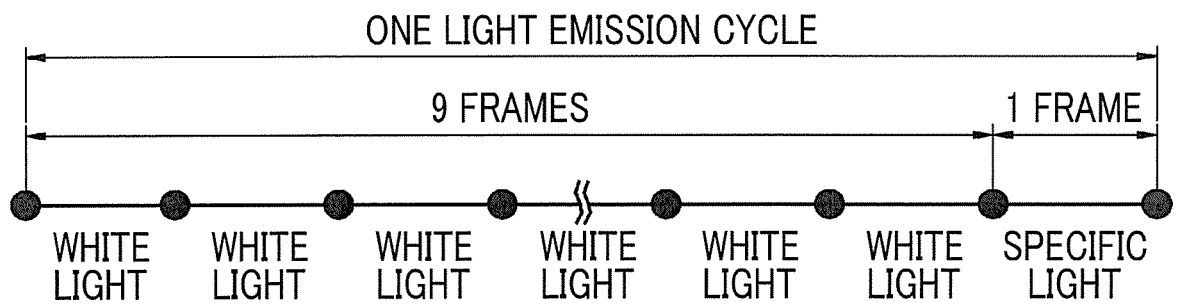
FIG. 3 is an explanatory diagram showing a first light emission pattern.

For example, as shown in FIG. 3, in a case where the number of light emission frames of white light is set to "9" and the number of light emission frames of specific light is set to "1" in one light emission cycle, as the first light emission pattern, white light is continuously emitted for "9" frames and then specific light is emitted for "1" frame. As the case where the first light emission pattern is set, there are a case of "not using of zooming", and a case where the light emission amount of white light or specific light exceeds a light emission amount threshold. Even in such a case, similar to the case where the moving speed of the endoscope 12 exceeds the speed threshold, since it is considered that the necessity for detecting a lesion area is low under a situation where a region with no lesion or a region where confirmation of a lesion is easy is observed, the first light emission pattern is set.

Further, in a case where the moving speed of the endoscope 12 is equal to or less than the speed threshold, the light source control unit 22 sets, as the specific light emission pattern, a second light emission pattern in which the number of light emission frames of specific light is greater than or the same as the number of light emission frames of white light in one light emission cycle, and performs light emission control on the basis of the second light emission pattern. In this manner, in a case where the moving speed of the endoscope 12 is equal to or less than the speed threshold, since it is considered that the necessity for detecting a lesion area is high under a situation where there is a possibility of a lesion, or a lesion is detected and examined, the second light emission pattern in which the number of light emission frames of specific light is high is set.

Figure 4:
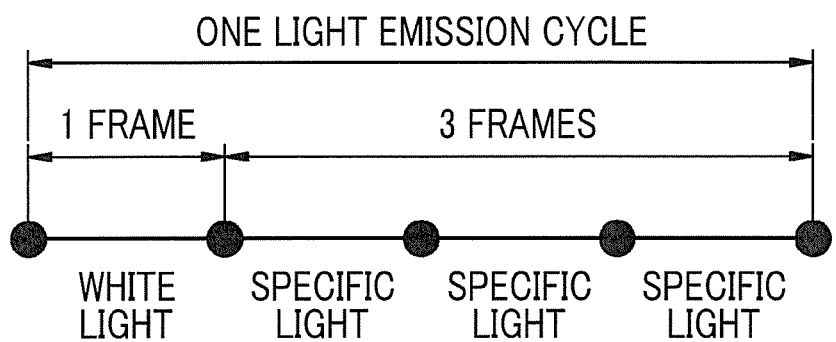
FIG. 4 is an explanatory diagram showing a second light emission pattern in which the number of light emission frames of specific light is greater than the number of light emission frames of white light in one light emission cycle.

For example, as shown in FIG. 4, in a case where the number of light emission frames of white light is set to "1" and the number of light emission frames of specific light is set to "3" in one light emission cycle, as the second light emission pattern, white light is emitted for "I" frame and then specific light is continuously emitted for "3" frames. As the case where the second light emission pattern is set, there are a case of "using of zooming", and a case where the light emission amount of white light or specific light is equal to or less than the light emission amount threshold. Even in such a case, similar to the case where the moving speed of the endoscope 12 is equal to or less than the speed threshold, since it is considered that the necessity for detecting a lesion area is high under a situation where there is a possibility of a lesion, or a lesion is detected and examined, the second light emission pattern is set.

Figure 5:
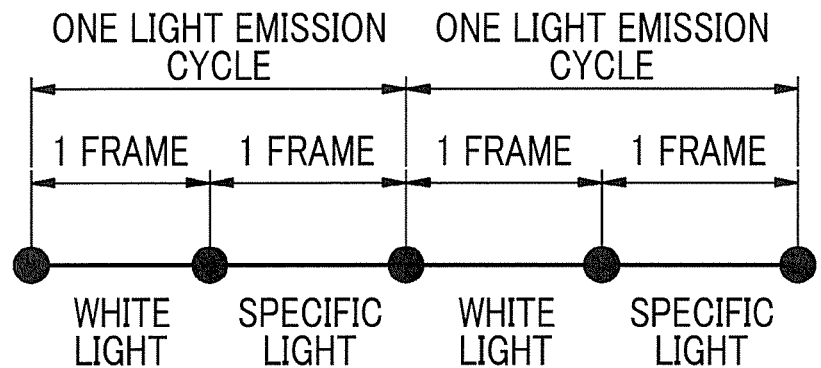
FIG. 5 is an explanatory diagram showing a second light emission pattern in which the number of light emission frames of white light is the same as the number of light emission frames of specific light in one light emission cycle.

In case of "not using of zooming" while the light emission amount of white light or specific light is equal to or less than the light emission amount threshold, it is preferable to set the second light emission pattern in which the number of light emission frames of white light is the same as the number of light emission frames of specific light. For example, as shown in FIG. 5, in a case where the number of light emission frames of white light is set to "I" and the number of light emission frames of specific light is set to "I" in one light emission cycle, as the second light emission pattern, white light and specific light are alternately emitted every frame. In the second light emission pattern, it is preferable to increase the number of light emission frames of specific light in one light emission cycle as the zoom magnification is increased in "using of zooming".

Figure 6:
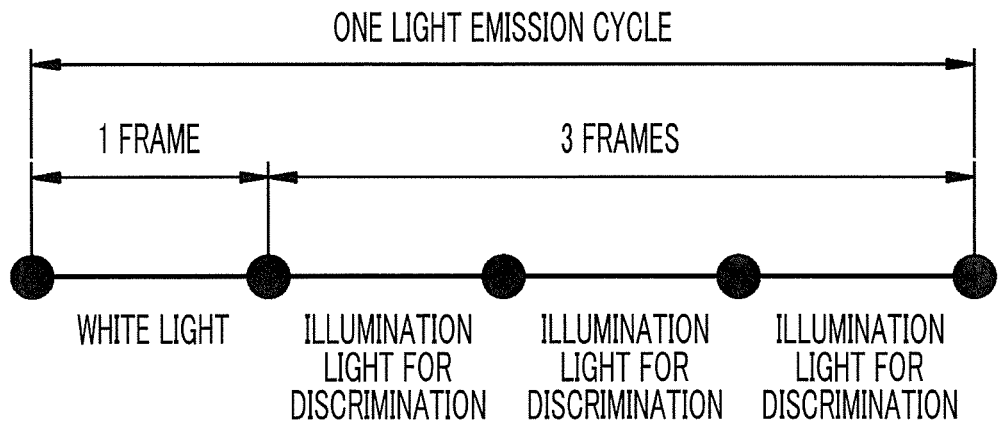
FIG. 6 is an explanatory diagram showing a second light emission pattern in which white light and illumination light for discrimination are emitted.

Further, in a case where the light emission amount of white light or specific light is equal to or less than the light emission amount threshold and in case of "using of zooming", since there is a possibility of performing discrimination processing by a discrimination unit 78, which will be described below, it is preferable to switch from specific light in which 450 nm is included in the peak wavelength to illumination light for discrimination in which 410 nm is included in the peak wavelength, in addition to making the number of light emission frames of specific light greater than or the same as the number of light emission frames of white light. In FIG. 6, in one light emission cycle, the number of light emission frames of white light is set to "1" and the number of light emission frames of illumination light for discrimination is set to "3". Here, specific light is suitable for detecting a lesion area (picking up a lesion area) as in screening, whereas illumination light for discrimination is suitable for discriminating a lesion area since illumination light for discrimination can clearly illuminate surface structures such as blood vessel structures or gland duct structures. Accordingly, in a case where observation is performed by enlarging a lesion area or the like by using zooming, it is preferable to perform illumination by switching from specific light to illumination light for discrimination. Without switching from specific light to illumination light for discrimination, illumination light for discrimination may be emitted in addition to specific light.

As shown in FIG. 2, the illumination light emitted from the light source unit 20 is incident on a light guide 41. The light guide 41 is built in the endoscope 12 and a universal cord (not shown), and propagates illumination light to a distal end portion 12d of the endoscope 12. The universal cord is a cord for connecting the endoscope 12 to the light source device 14 and the processor device 16. It is possible to use a multi-mode fiber as the light guide 41. As an example, it is possible to use a small-diameter fiber cable of which a core diameter is 105 µm, a cladding diameter is 125 µm, and a diameter including a protective layer as an outer skin is φ0.3 mm to φ0.5 mm.

An illumination optical system 30a and an imaging optical system 30b are provided in the distal end portion 12d of the endoscope 12. The illumination optical system 30a has an illumination lens 45, and illumination light is emitted toward the observation target through the illumination lens 45. The imaging optical system 30b has an objective lens 46, a zoom lens 47, and an image sensor 48. The image sensor 48 images the observation target using reflected light or the like (including scattered light, fluorescence emitted from the observation target, fluorescence due to medicine administered to the observation target, and the like in addition to the reflected light) of the illumination light that returns from the observation target through the objective lens 46 and the zoom lens 47.

The zoom lens 47 is moved by operating the zoom operation part 13, thereby enlarging or reducing the observation target to be imaged by using the image sensor 48. Zoom information relating to zooming of enlarging the observation target by the zoom lens 47 is transmitted from a zoom information output unit 49 to the light source control unit 22 of the light source device 14. As the zoom information, for example, "not using of zooming" is set in a case where the zoom lens 47 is positioned at a wide end so that the observation target is not enlarged. Meanwhile, "using of zooming" is set in a case where the zoom lens 47 is moved from the wide end to a telephoto end so that the observation target is enlarged. Further, in the zoom information, in "using of zooming", information regarding the zoom magnification of the zoom lens 47 is also included.

The image sensor 48 is, for example, a color sensor having primary color system color filters, and comprises three kinds of pixels of a blue pixel (B pixel) having a blue color filter, a green pixel (G pixel) having a green color filter, and a red pixel (R pixel) having a red color filter. The blue color filter mainly transmits violet to blue light. The green color filter mainly transmits green light. The red color filter mainly transmits red light. In a case where the observation target is imaged using the primary color system image sensor 48 as described above, three types of images of a blue image (B image) obtained from the B pixel, a green image (G image) obtained from the G pixel, and a red image (R image) obtained from the R pixel can be simultaneously obtained at maximum.

As the image sensor 48, it is possible to use a charge coupled device (CCD) sensor or a complementary metal oxide semiconductor (CMOS) sensor. Although the image sensor 48 of the embodiment is a primary color system color sensor, it is also possible to use a complementary color system color sensor. For example, the complementary color system color sensor has a cyan pixel in which a cyan color filter is provided, a magenta pixel in which a magenta color filter is provided, a yellow pixel in which a yellow color filter is provided, and a green pixel in which a green color filter is provided. Images obtained from the pixels of the respective colors described above in case of using the complementary color system color sensor can be converted into the B image, the G image, and the R image by performing complementary color-primary color conversion. Instead of the color sensor, a monochrome sensor in which no color filter is provided can be used as the image sensor 48. In this case, it is possible to obtain images of the respective colors by sequentially imaging the observation target using illumination light of respective colors such as BGR.

The processor device 16 includes a central control unit 52, an image acquisition unit 54, an image processing unit 61, and a display control unit 66. The central control unit 52 performs overall control of the endoscope system 10, such as synchronization control of irradiation timing of illumination light and imaging timing. In a case where various settings are input using the user interface 19 or the like, the central control unit 52 inputs the input various settings to each unit of the endoscope system 10, such as the light source control unit 22, the image sensor 48, or the image processing unit 61.

The image acquisition unit 54 acquires an image in which the observation target is imaged, from the image sensor 48. Since the image acquired by the image acquisition unit 54 is an image obtained by a medical apparatus, such as the endoscope 12, the image is referred to as a medical image. The image acquisition unit 54 includes a digital signal processor (DSP) 56, a noise reduction unit 58, and a conversion unit 59, and performs various kinds of processing on the acquired medical image using these as necessary. The DSP 56 performs various kinds of processing, such as defect correction processing, offset processing, gain correction processing, linear matrix processing, gamma conversion processing, demosaicing processing, and YC conversion processing, on the acquired medical image as necessary.

The defect correction processing is processing for correcting the pixel value of each pixel corresponding to the defective pixel of the image sensor 48. The offset processing is processing for setting an accurate zero level by reducing a dark current component from the image subjected to the defect correction processing. The gain correction processing is processing for adjusting a signal level of each image by multiplying the image subjected to the offset processing by the gain. The linear matrix processing is processing for improving the color reproducibility of the image subjected to the offset processing, and the gamma conversion processing is processing for adjusting the brightness or the saturation of the image after the linear matrix processing.

In a case where the image sensor 48 is a color sensor, demosaicing processing is performed. The demosaicing processing (also referred to as isotropic processing or demosaicing) is processing for interpolating the pixel values of missing pixels, and is performed on the image after the gamma conversion processing. The missing pixel is a pixel having no pixel value due to the arrangement of color filters (since pixels of other colors are arranged in the image sensor 48). For example, since the B image is an image obtained by imaging the observation target in the B pixel, a pixel at a position corresponding to the G pixel or the R pixel has no pixel value. The demosaicing processing is for generating the pixel values of pixels at the positions of the G and R pixels of the image sensor 48 by interpolating the B image. The YC conversion processing is processing for converting the image after the demosaicing processing into a brightness channel Y, a color difference channel Cb, and a color difference channel Cr.

The noise reduction unit 58 performs noise reduction processing on the brightness channel Y, the color difference channel Cb, and the color difference channel Cr using, for example, a moving average method or a median filter method. The conversion unit 59 reconverts the brightness channel Y, the color difference channel Cb, and the color difference channel Cr after the noise reduction processing into images of the respective colors of BGR.

The image processing unit 61 performs various kinds of image processing on the medical image acquired by the image acquisition unit 54. In the image processing unit 61, the types of image processing performed in the normal mode and the special mode are different. In the normal mode, a white light image is generated by performing image processing corresponding to white light (white light image processing), on the medical image obtained at the time of illumination of white light. Further, in the special mode, a white light image is generated by performing image processing corresponding to white light (white light image processing), on the medical image obtained at the time of illumination of white light. Meanwhile, a region of interest is detected from a specific light image as a medical image obtained at the time of illumination of specific light, and discrimination processing relating to a lesion is performed on the detected region of interest. The detection of the region of interest and the discrimination processing will be described below in detail. Then, the detection result of the region of interest and the result of the discrimination processing are reflected in the white light image, and thereby a region-of-interest display image is generated. The display control unit 66 converts the white light image or the region-of-interest display image transmitted from the image processing unit 61 into a format suitable for the display on the monitor 18, and outputs the conversion result to the monitor 18. In this manner, the white light image or the region-of-interest display image is displayed on the monitor 18.

Figure 7:
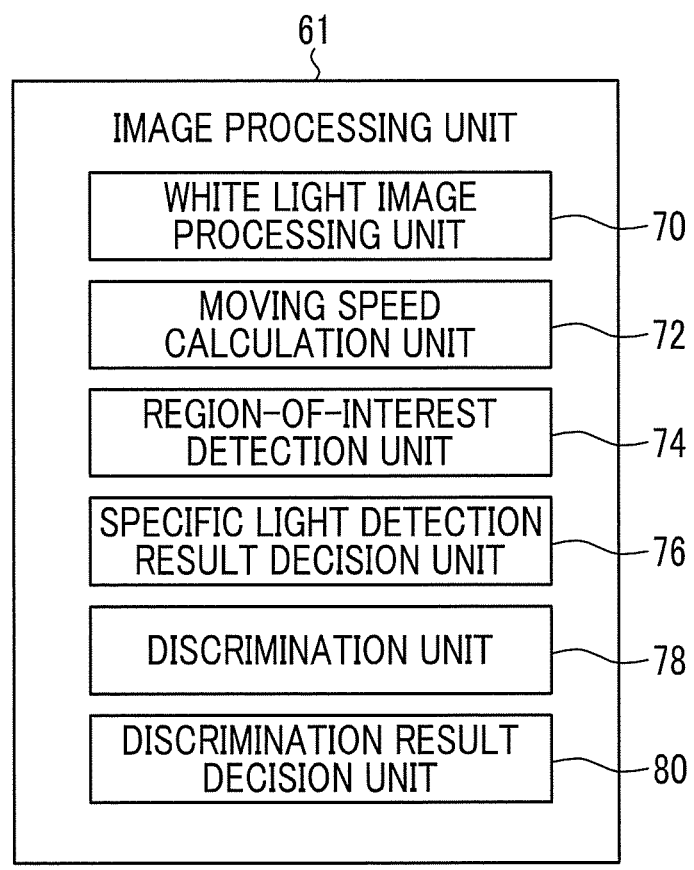
FIG. 7 is a block diagram showing a function of an image processing unit.

As shown in FIG. 7, the image processing unit 61 comprises a white light image processing unit 70, a moving speed calculation unit 72, a region-of-interest detection unit 74, a specific light detection result decision unit 76, a discrimination unit 78, and a discrimination result decision unit 80. The white light image processing unit 70 performs the white light image processing as the image processing corresponding to the white light, on the medical image obtained at the time of illumination of white light in the normal mode or the special mode. In this manner, the white light image is obtained. In the white light image processing, structure emphasizing processing for emphasizing the structure on the observation target is included in addition to color adjustment processing for approximating the color to the color of the observation target.

The moving speed calculation unit 72 calculates the moving speed of the endoscope 12 using any of the white light image or the specific light image. The calculated moving speed of the endoscope 12 is transmitted to the light source control unit 22 of the light source device 14. The moving speed of the endoscope 12 refers to a speed at which the distal end portion of the endoscope 12 in which the image sensor 48 (corresponding to the "imaging unit" of the invention) is built is moved by pushing or inserting the insertion part 12a of the endoscope 12 into the lumen and other operations of the endoscope 12 by the user. As the calculation method of the moving speed, for example, a moving vector is calculated from a plurality of white light images or specific light images with different image acquisition timings, and the moving speed of the endoscope 12 is calculated on the basis of the moving vector. The moving speed of the endoscope 12 becomes increased as the moving vector is increased. The "observation situation acquisition unit" of the invention corresponds to the "moving speed calculation unit 72".

Figure 8:
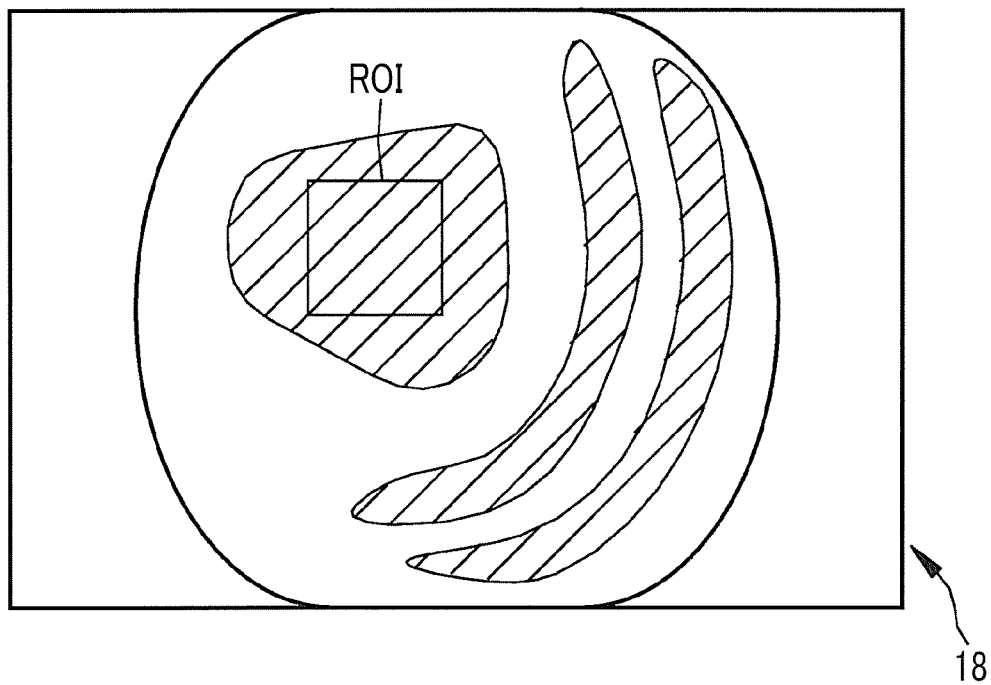
FIG. 8 is an image diagram showing a white light image in which a region of interest ROI is displayed in a superimposed manner.

The region-of-interest detection unit 74 performs region-of-interest detection processing for detecting a region of interest to be noticed as a target of inspection or diagnosis from the specific light image. In the region-of-interest detection processing, a feature quantity is calculated from the specific light image, and a region where the calculated feature quantity is within a specific range is detected as the region of interest. The detected region of interest is displayed as rectangular region ROI on the white light image as shown in FIG. 8. Note that, the region of interest detected by the region-of-interest detection unit 74 is not limited to a two-dimensional region such as the surface of the observation target. For example, in addition to the surface of the observation target, a three-dimensional region in a depth direction (infiltration) of the observation target may be detected as the region of interest.

Here, the feature quantity may be a blood vessel index value relating to blood vessels or a gland duct index value relating to gland duct structures which will be described below. As the feature quantity, for example, a feature quantity obtained by color information and the gradient of the pixel values of the specific light image in addition to performing convolutional neural network on the specific light image may be used. The gradient of the pixel values or the like changes depending on, for example, the shape of the subject (global undulations of a mucous membrane or local depressions or bumps), color (color such as whitening due to inflammation, bleeding, redness, or atrophy), a feature of a tissue (thickness, depth, or density of a blood vessel, or a combination thereof), or a feature of a structure (pit pattern or the like).

Further, the region of interest detected by the region-of-interest detection unit 74 is a region including a lesion area represented by a cancer, a benign tumor area, an inflammation area (including a portion with changes such as bleeding or atrophy in addition to a so-called inflammation), a cauterization scar due to heating or a marking area marked by coloring with a coloring agent, a fluorescent agent, or the like, or a biopsy area where biopsy inspection (so called biopsy) is performed. That is, a region including a lesion, a region having a possibility of a lesion, a region where any treatment such as a biopsy is performed, a treatment tool such as clips or forceps, a region which is required to be observed in detail regardless of a possibility of a lesion, such as a dark region (back of folds, a region where observation light is difficult to reach due to the depth of the lumen), or the like can be a region of interest. In the endoscope system 10, the region-of-interest detection unit 74 detects a region including at least one of a lesion area, a benign tumor area, an inflammation area, a marking area, or a biopsy area, as the region of interest.

Here, in a case where one specific light image is obtained with the light emission frame of specific light being "1" in one light emission cycle, the region of interest detected from the one specific light image is displayed in a superimposed manner as it is on the white light image. Meanwhile, in a case where a plurality of specific light images are obtained with a plurality of light emission frames of specific light in one light emission cycle, the region-of-interest detection processing is performed on the specific light images, and it is preferable to decide a specific light detection result to be reflected in the white light image on the basis of the results of the region-of-interest detection processing on the specific light images. Even in a case where the light emission amount of white light or specific light is low, it is possible to ensure robustness against noise by deciding one specific light detection result from a plurality of detection results of the region of interest. The detection result processing for deciding the specific light detection result is performed by the specific light detection result decision unit 76. The specific light detection result decided by the specific light detection result decision unit 76 is reflected in the white light image.

In a case where both the result with the detection of the region of interest and the results without the detection of the region of interest for the same region are obtained from the plurality of specific light images in one light emission cycle, the specific light detection result decision unit 76 decides, as the specific light detection result, any of the results with the detection of the region of interest or the results without the detection of the region of interest by the majority based on the number of results with the detection of the region of interest and the number of results without the detection of the region of interest.

Figure 9:
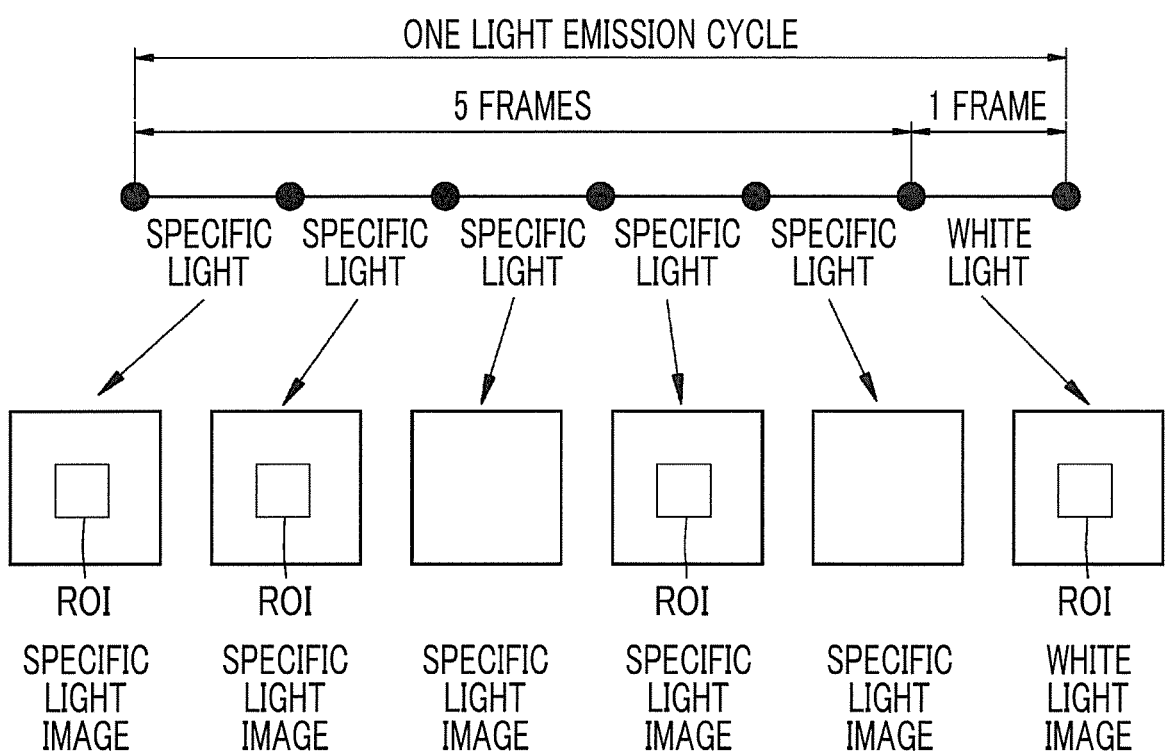
FIG. 9 is an explanatory diagram showing that a specific light detection result is decided by a majority.

For example, in a case where five specific light images are obtained in one light emission cycle as shown in FIG. 9, when the number of specific light images having the result with the detection of the region of interest is "3" and the number of specific light images having the result without the detection of the region of interest is "2" for the same region, the result with the detection of the region of interest is decided as the specific light detection result by the majority. In a case where the number of results with the detection of the region of interest and the number of the results without the detection of the region of interest are the same, it is preferable to use the result with the detection of the region of interest as the specific light detection result.

Figure 10:
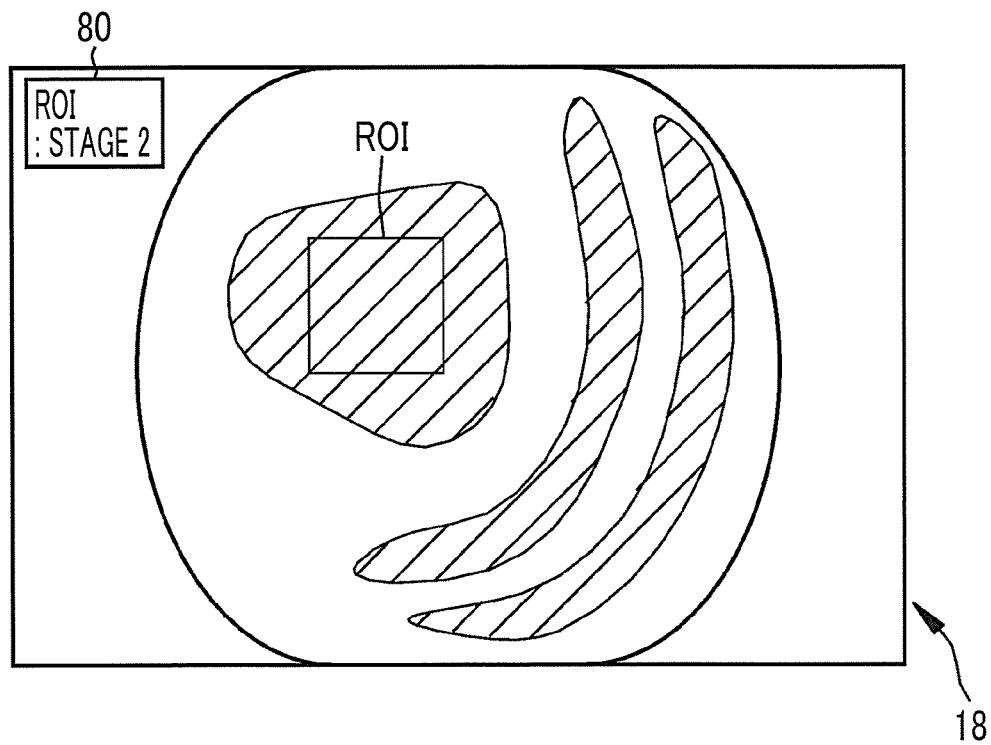
FIG. 10 is an image diagram showing a white light image in which a region of interest ROI is displayed in a superimposed manner and a discrimination result.

The discrimination unit 78 calculates various index values from the region of interest detected by the region-of-interest detection unit 74, and performs the discrimination processing for discriminating the observation target included in the region of interest on the basis of the calculated various index values. As the various index values, a blood vessel index value relating to blood vessels such as a blood vessel density or a blood vessel running pattern, or a gland duct index value relating to gland duct structures are included. As the result of the discrimination processing, a progress degree (stage) of a lesion area or the like is exemplified. As shown in FIG. 10, the result of the discrimination processing is displayed on the monitor 18 in correspondence to the region of interest ROI ("stage 2" in FIG. 10).

Here, in a case where the discrimination processing is performed on one region of interest detected from one specific light image obtained with the light emission frame of specific light being "1" in one light emission cycle, the result of the discrimination processing is displayed. Meanwhile, in a case where a plurality of regions of interest are detected from a plurality of specific light images obtained with a plurality of light emission frames of specific light in one light emission cycle, the discrimination processing is performed on the respective regions of interest, and it is preferable to decide a specific light discrimination result to be displayed on the monitor 18, on the basis of the result of the discrimination processing on the respective regions of interest. Even in a case where the light emission amount of white light or specific light is low, it is possible to ensure robustness against noise by deciding one specific light discrimination result from a plurality of results of the discrimination processing. The discrimination result processing for deciding the specific light discrimination result is performed by the discrimination result decision unit 80. The specific light discrimination result decided by the discrimination result decision unit 80 is displayed on the monitor 18 together with the white light image where the region of interest ROI is displayed in a superimposed manner.

Figure 11:
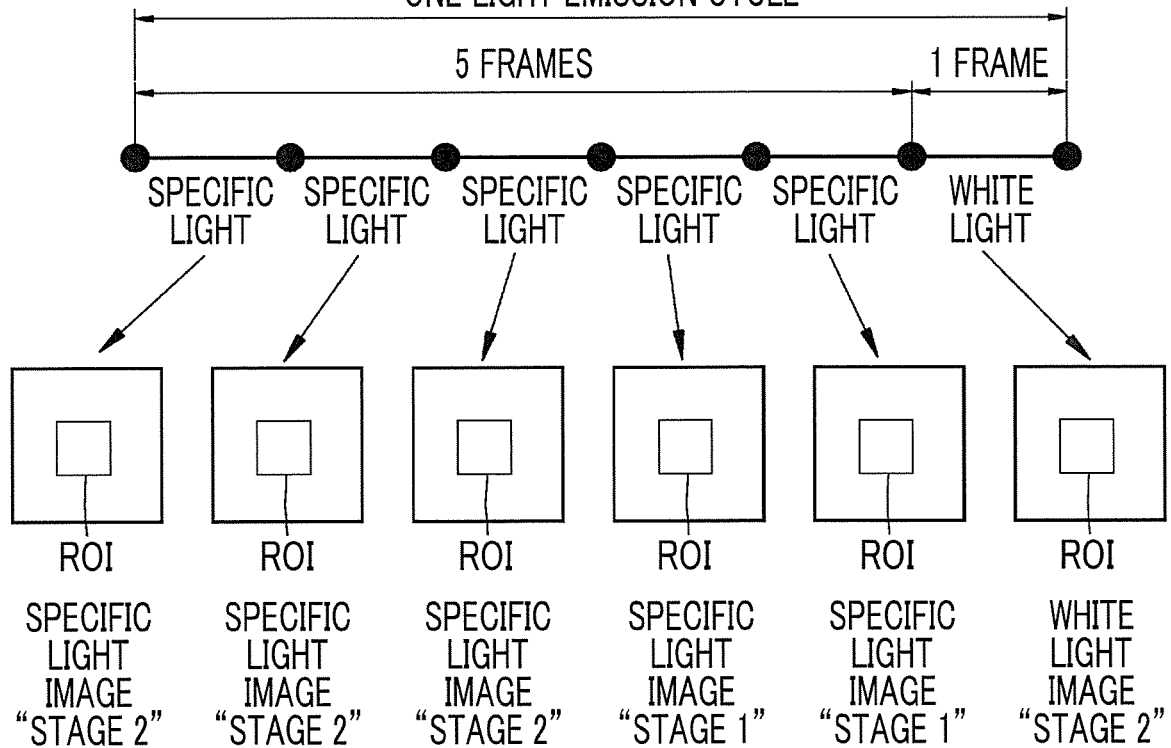
FIG. 11 is an explanatory diagram showing that a specific light discrimination result is decided by a majority.

In a case where a plurality of regions of interest are detected from a plurality of specific light images in one light emission cycle and the discrimination processing is performed on the respective regions of interest, the discrimination result decision unit 80 may decide the specific light discrimination result by the majority based on the results of the discrimination processing on the respective regions of interest. For example, as shown in FIG. 11, in a case where five specific light images are obtained in one light emission cycle and one region of interest is detected from each of the specific light images, when the number of regions of interest with the discrimination processing result of "stage 2" is "3" and the number of regions of interest with the discrimination processing result of "stage 1" is "2", "stage 2" is decided as the specific light discrimination result. The "stage" is determined in advance according to the state of the observation target such as a lesion area, and in general, the progress degree of the lesion is increased as the number attached to the "stage" is increased.

Figure 12:
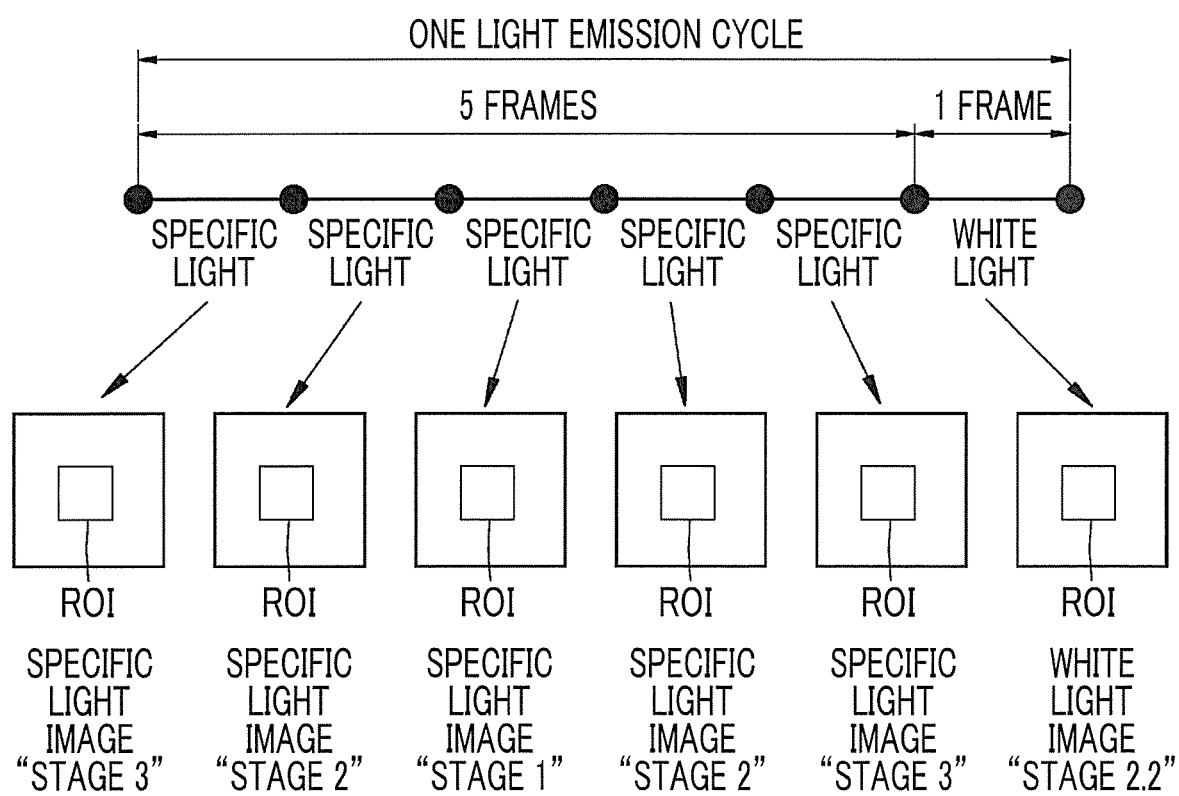
FIG. 12 is an explanatory diagram showing that a specific light discrimination result is decided by averaging.

Further, in a case where a plurality of regions of interest are detected from a plurality of specific light images in one light emission cycle and the discrimination processing is performed on the respective regions of interest, the discrimination result decision unit 80 may decide a result obtained by averaging the results of the discrimination processing on the respective regions of interest, as the specific light discrimination result. For example, as shown in FIG. 12, in a case where five specific light images are obtained in one light emission cycle and one region of interest is detected from each of the specific light images, when the number of regions of interest with the discrimination processing result of "stage 3" is "2", the number of regions of interest with the discrimination processing result of "stage 2" is "2", and the number of regions of interest with the discrimination processing result of "stage 1" is "1", the averaged result "2.2 (=(3×2+2×2+1)/5)" is decided as the specific light discrimination result. It is preferable that the averaged result is rounded off (for example, in case of FIG. 12, the specific light discrimination result becomes "2" by rounding off).

Figure 13:
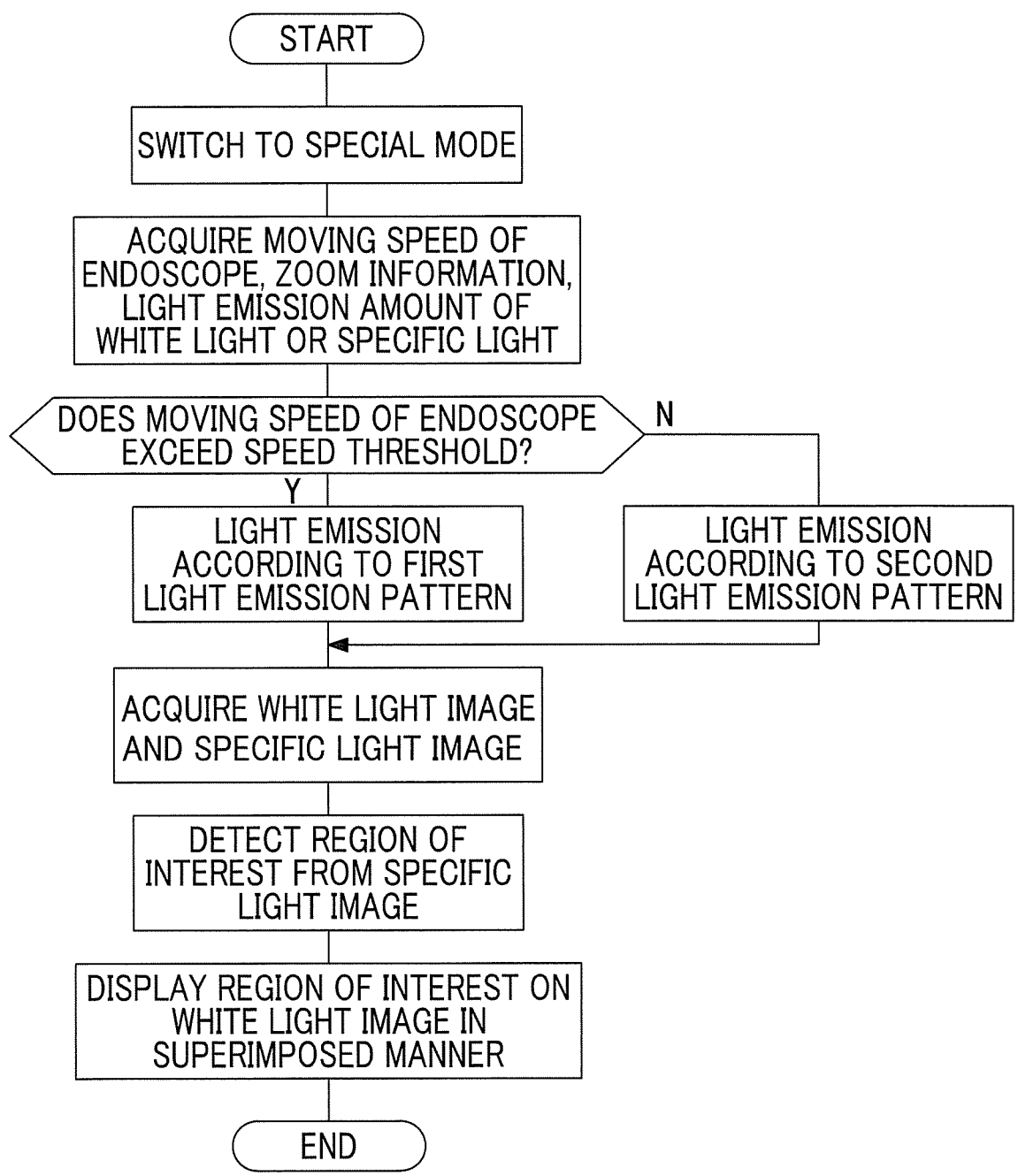
FIG. 13 is a flowchart showing a series of flows in a special mode.

Next, the flow in the special mode will be described with reference to the flowchart shown in FIG. 13. When switching to the special mode, the moving speed calculation unit 72 calculates the moving speed of the endoscope 12. The zoom information output unit 49 outputs the zoom information relating to the zooming of enlarging the observation target. Further, the light emission amount measurement unit 21 measures the light emission amount of white light or the light emission amount of specific light.

Then, any one of the first light emission pattern in which the number of light emission frames of white light is greater than the number of light emission frames of specific light in one light emission cycle or the second light emission pattern in which the number of light emission frames of specific light is greater than the number of light emission frames of white light in one light emission cycle is decided according to at least one of the moving speed of the endoscope 12, the zoom information, or the light emission amount of white light or specific light. In a case where the moving speed of the endoscope 12 exceeds the speed threshold, in case of "not using of zooming", or in a case where the light emission amount of white light or specific light exceeds the light emission amount threshold, the first light emission pattern is set. Then, the light source control unit 22 performs light source control according to the first light emission pattern.

In contrast, in a case where the moving speed of the endoscope 12 is equal to or less than the speed threshold, in case of "using of zooming", or in a case where the light emission amount of white light or specific light is equal to or less than the light emission amount threshold, the second light emission pattern is set. Then, the light source control unit 22 performs the light source control according to the second light emission pattern.

The white light image is acquired by imaging the observation target illuminated with white light. In addition, the specific light image is acquired by imaging the observation target illuminated with specific light. The region-of-interest detection unit 74 detects the region of interest ROI from the specific light image. The detected region of interest is displayed on the white light image in a superimposed manner. In a case where specific light for one frame is emitted in one light emission cycle and the specific light image for one frame is obtained, the region of interest detected from the specific light image for the one frame is displayed on the white light image in a superimposed manner. Meanwhile, in a case where specific light for a plurality of frames is emitted in one light emission cycle and the specific light images for the plurality of frames are obtained, the region-of-interest detection processing is performed on the respective specific light images. Then, the specific light detection result decision unit 76 decides the specific light detection result to be reflected in the white light image on the basis of the result of the region-of-interest detection processing on the respective specific light images. The specific light detection result is reflected in the white light image.

In the embodiment, the number of light emission frames of white light or the number of light emission frames of specific light is controlled according to whether the moving speed of the endoscope 12 exceeds the speed threshold. However, a learning machine may learn a relationship between the moving speed of the endoscope 12 and the number of light emission frames of white light or the number of light emission frames of specific light using a method such as artificial intelligence (AI) in advance, and the number of light emission frames of white light or the number of light emission frames of specific light may be decided by inputting the moving speed of the endoscope 12 to the learning machine. Similar to the moving speed of the endoscope 12, the learning machine may learn a relationship between the zoom information or the light emission amount of white light or specific light and the number of light emission frames of white light or the number of light emission frames of specific light in advance, and the number of light emission frames of white light or the number of light emission frames of specific light may be decided by inputting the zoom information or the light emission amount of white light or specific light to the learning machine. As described in the embodiment, the number of light emission frames of white light or the number of light emission frames of specific light may be decided by comprehensively considering the moving speed of the endoscope 12, the zoom information, or the light emission amount of white light or specific light.

Figure 14:
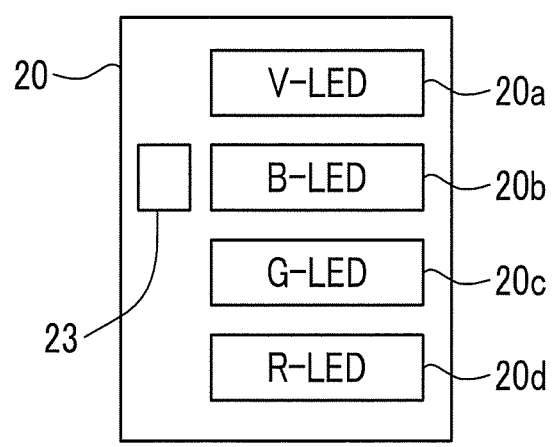
FIG. 14 is a block diagram showing a light source unit comprising a plurality of LEDs.

In the embodiment, it is preferable that illumination light is emitted by using LEDs of four colors, such as a violet light emitting diode (V-LED) 20a, a blue light emitting diode (B-LED) 20b, a green light emitting diode (G-LED) 20c, and a red light emitting diode (R-LED) 20d, and a wavelength cut filter 23 as the light source unit 20, as shown in FIG. 14.

The V-LED 20a emits violet light V in a wavelength range of 380 nm to 420 nm. The B-LED 20b emits blue light B in a wavelength range of 420 nm to 500 nm. Among the blue light B emitted from the B-LED 20b, at least light in a wavelength range on the longer wavelength side than a peak wavelength of 450 nm is cut by the wavelength cut filter 23. In this manner, blue light Bx transmitted through the wavelength cut filter 23 is within a wavelength range of 420 nm to 460 nm. The reason of cutting light in a wavelength range on the longer wavelength side than 460 nm is that light in a wavelength range on the longer wavelength side than 460 nm is a factor reducing a blood vessel contrast of the blood vessel as the observation target. The wavelength cut filter 23 may attenuate light in a wavelength range on the longer wavelength side than 460 nm instead of cutting light in a wavelength range on the longer wavelength side than 460 nm. The G-LED 20c emits green light G having a wavelength range of 480 nm to 600 nm. The R-LED 20d emits red light R having a wavelength range of 600 nm to 650 nm.

Figure 15:
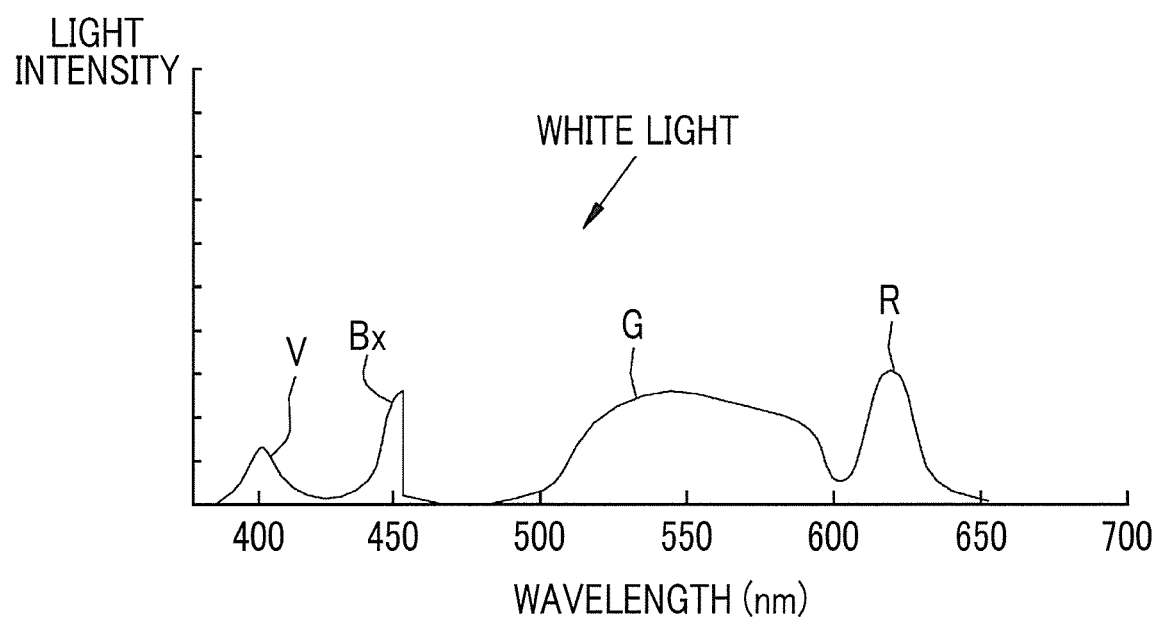
FIG. 15 is a graph showing a spectrum of white light obtained by emission of a plurality of LEDs.

In the normal mode, all of the V-LED 20a, the B-LED 20b, the G-LED 20c, and the R-LED 20d are turned on. In this manner, as shown in FIG. 15, the light source device 14 emits white light including violet light V, blue light Bx, green light G, and red light R. Since white light has an intensity of a certain level or greater from the blue-light wavelength range to the red-light wavelength range, white light is almost white.

Figure 16:
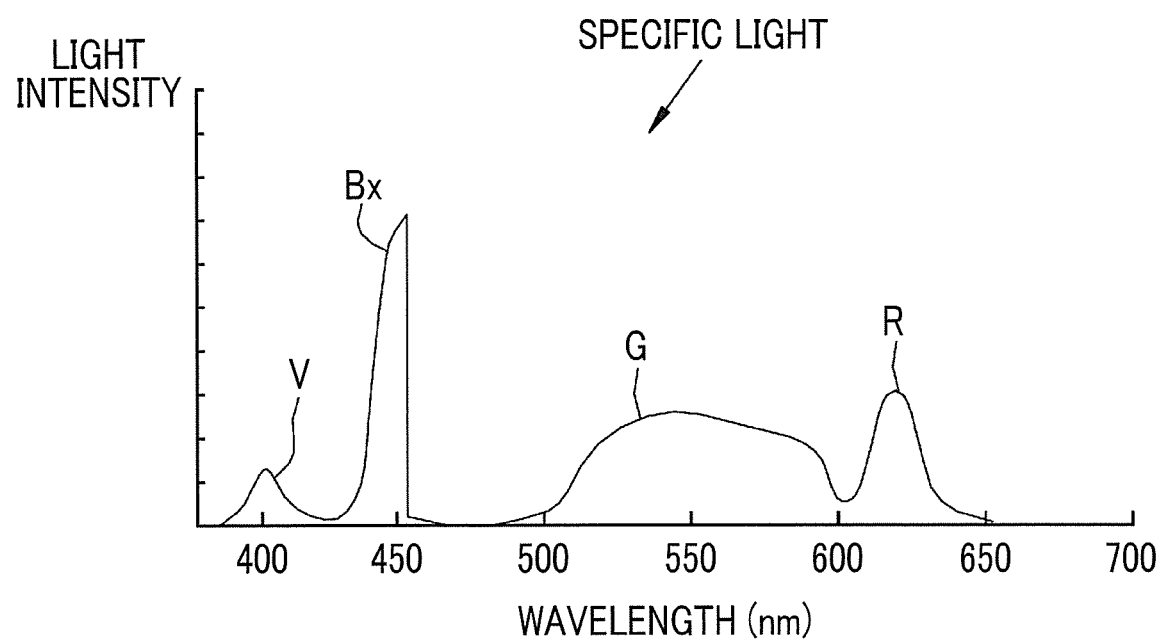
FIG. 16 is a graph showing a spectrum of specific light obtained by emission of a plurality of LEDs.

In the special mode, light emission control for the V-LED 20a, the B-LED 20b, the G-LED 20c, and the R-LED 20d is performed such that white light or specific light is emitted according to a specific light emission pattern. In case of emitting white light, as described above, white light having a spectrum shown in FIG. 15 is emitted. Meanwhile, in case of emitting specific light, specific light in which the light emission amount of blue light Bx is greater than any light emission amount of violet light V, green light G, and red light R is emitted as shown in FIG. 16.

Figure 17:
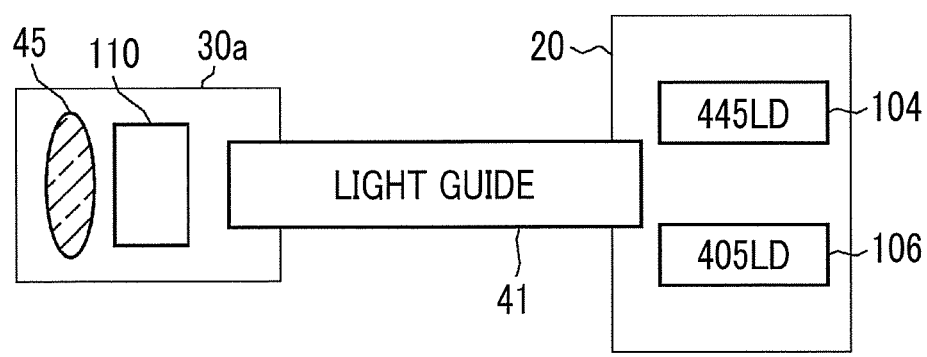
FIG. 17 is a block diagram showing a light source unit comprising a laser light source, and a phosphor.

In the embodiment, illumination light may be emitted using the laser light source and a phosphor. In this case, as shown in FIG. 17, the light source unit 20 is provided with a blue laser light source (indicated as "445LD", LD indicates a "laser diode") 104 that emits blue laser light having a peak wavelength of 445±10 nm, and a blue-violet laser light source (indicated as "405LD") 106 that emits blue-violet laser light having a peak wavelength of 405±10 nm.

The illumination optical system 30a is provided with a phosphor 110 on which blue laser light or blue-violet laser light is incident from the light guide 41, in addition to the illumination lens 32. The phosphor 110 is excited by blue laser light to emit fluorescence. In addition, some of blue laser light is transmitted without exciting the phosphor 110. Blue-violet laser light is transmitted without exciting the phosphor 110. Light from the phosphor 110 illuminates the body of the observation target via the illumination lens 32.

Figure 18:
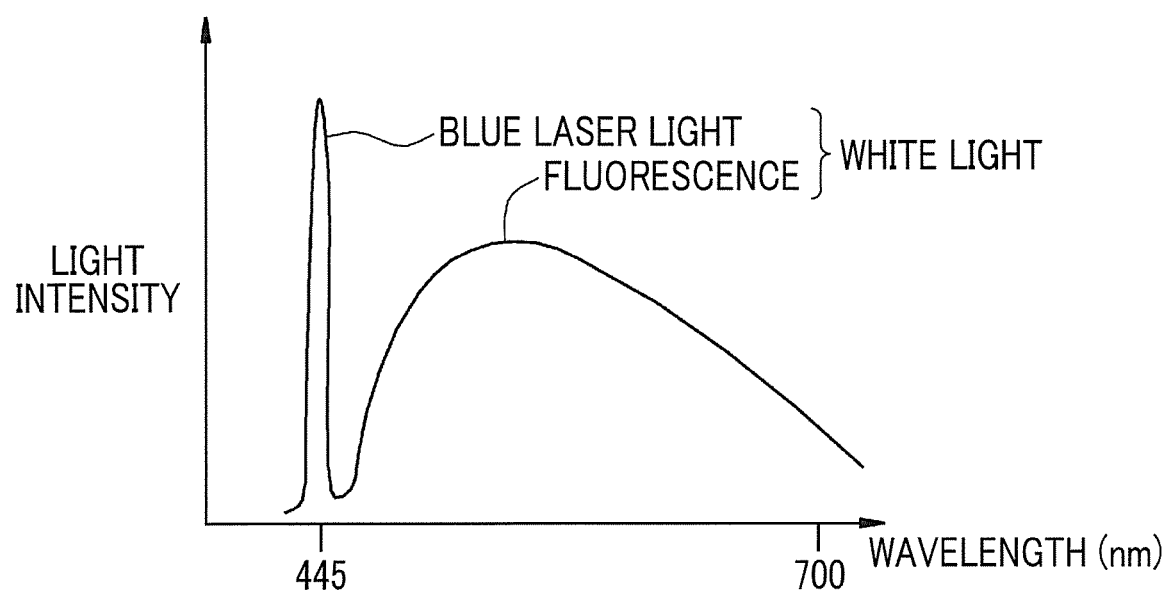
FIG. 18 is a graph showing a spectrum of white light emitted using a laser light source and a phosphor.
Figure 19:
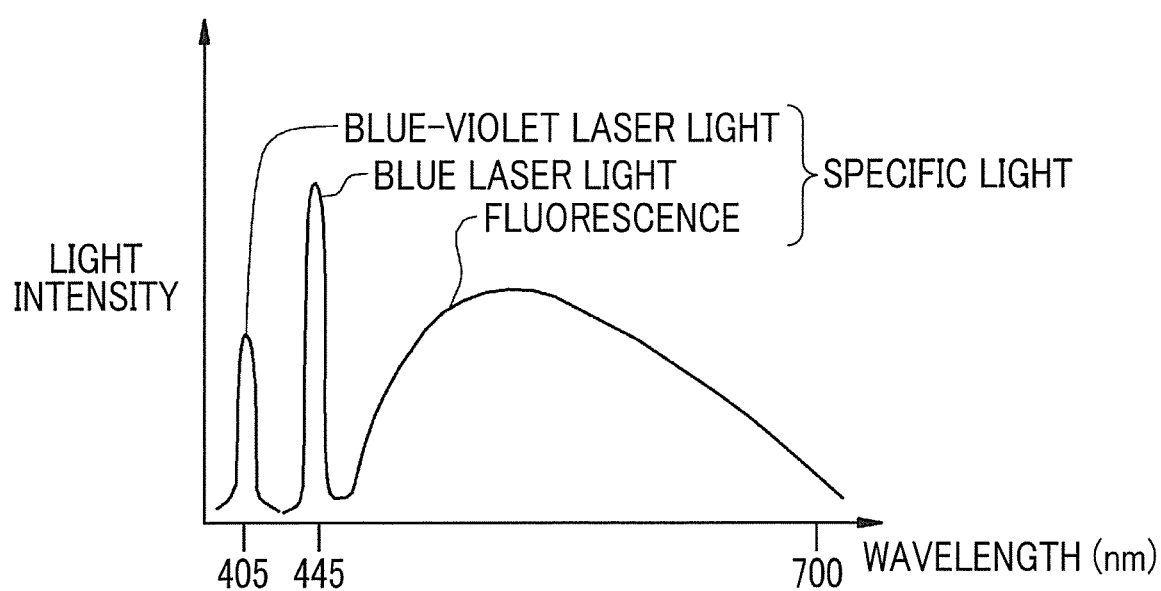
FIG. 19 is a graph showing a spectrum of specific light emitted using a laser light source and a phosphor.

Here, in the normal mode, the blue laser light source 104 is turned on so that blue laser light is mainly incident on the phosphor 110, and thus white light in which blue laser light and fluorescence emitted from the phosphor 110 excited by blue laser light are combined, as shown in FIG. 18 is emitted. Meanwhile, in the special mode, light emission control for the blue laser light source 104 and the blue-violet laser light source 106 is performed such that white light or specific light is emitted according to a specific light emission pattern. In case of emitting white light, as described above, white light having a spectrum shown in FIG. 18 is emitted. Meanwhile, in case of emitting specific light, the blue laser light source 104 and the blue-violet laser light source 106 are turned on so that both blue-violet laser light and blue laser light are incident on the phosphor 110. In this manner, specific light in which blue-violet laser light, blue laser light, and fluorescence emitted from the phosphor 110 excited by blue laser light are combined, as shown in FIG. 19 is emitted.

It is preferable that the half width of blue laser light or blue-violet laser light is about ±10 nm. As the blue laser light source 104 and the blue-violet laser light source 106, broad area type InGaN laser diodes can be used, and InGaNAs laser diodes and GaNAs laser diodes can also be used. A configuration using a light emitter such as a light emitting diode may be used as the light source.

It is preferable to use the phosphor 110 configured to include a plurality of types of phosphors that absorb some of blue laser light to emit light from green to yellow by excitation (for example, YAG phosphor or phosphor such as BAM ($BaMgAl_{10}O_{17}$)). In a case where a semiconductor light emitting element is used as an excitation light source of the phosphor 110 as in this configuration example, it is possible to obtain high intensity white light with high luminous efficiency, to easily adjust the intensity of white light, and suppress changes in color temperature and chromaticity of white light to be small.

Figure 20:
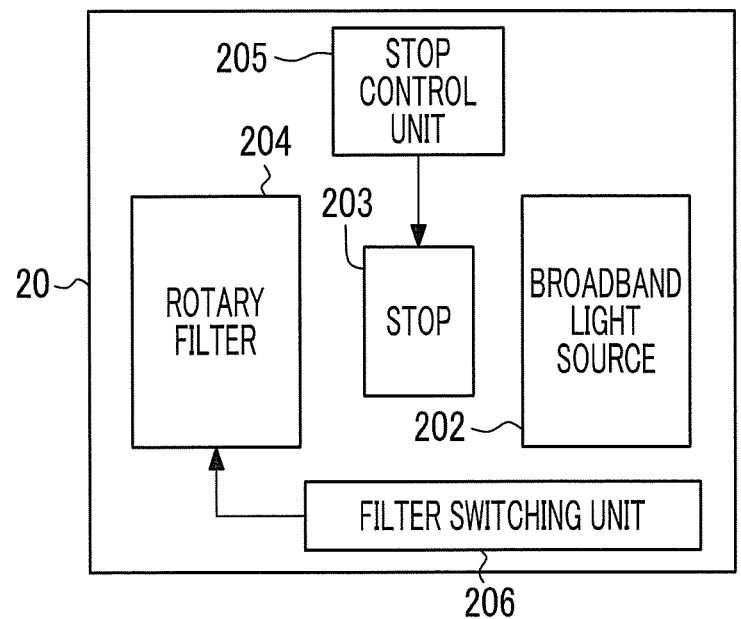
FIG. 20 is a block diagram showing a light source unit comprising a broadband light source and a rotary filter.

In the embodiment, illumination light may be emitted using a broadband light source such as a xenon lamp and a rotary filter. In this case, as shown in FIG. 20, a broadband light source 202, a rotary filter 204, and a filter switching unit 206 are provided in the light source unit 20. Further, a stop 203 is provided between the broadband light source 202 and the rotary filter 204, and the area of the opening of the stop 203 is adjusted by a stop control unit 205. The stop control unit 205 controls the stop 203 on the basis of dimming signals from the processor device 16.

The broadband light source 202 is a xenon lamp, a white LED, or the like, and emits broadband light having a wavelength range from blue to red. The rotary filter 204 comprises a normal mode filter 210 provided on the inner side closest to the rotary shaft, and a special mode filter 212 provided on the outer side of the normal mode filter 210 (refer to FIG. 21).

The filter switching unit 206 moves the rotary filter 204 in a radial direction. Specifically, in a case where the normal mode is set by a mode switching unit 13c, the filter switching unit 206 inserts the normal mode filter 210 to a light path of white light. In a case where the special mode is set, the filter switching unit 206 inserts the special mode filter 212 to the light path of white light.

Figure 21:
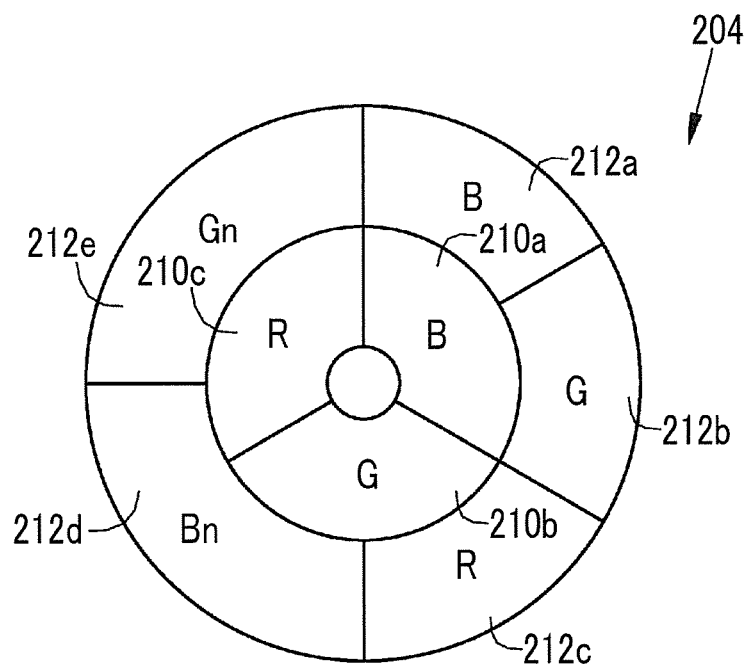
FIG. 21 is a plan view showing a rotary filter.

As shown in FIG. 21, the normal mode filter 210 is provided with a B filter 210a, a G filter 210b, and an R filter 210c along the circumferential direction. The B filter 210a transmits broadband blue light B having a wavelength range of 400 nm to 500 nm among broadband light. The G filter 210b transmits green light G among broadband light. The R filter 210c transmits red light R among broadband light. Accordingly, in the normal mode, as white light, blue light B, green light G, and red light R are sequentially emitted toward the observation target by the rotation of the rotary filter 204.

The special mode filter 212 is provided with a B filter 212a, a G filter 212b, an R filter 212c, a Bn filter 212d, and a Gn filter 212e along the circumferential direction. The B filter 212a transmits blue light B similarly to the B filter 210a. The G filter 212b transmits green light G similarly to the G filter 210b. The R filter 212c transmits red light R similarly to the R filter 210c. The Bn filter 212d transmits blue narrow-band light Bn having a wavelength range of 400 nm to 450 nm among broadband light. The Gn filter 212e transmits green light G among broadband light.

Accordingly, in the special mode, as white light, blue light B, green light G, and red light R are sequentially emitted toward the observation target by the rotation of the rotary filter 204. After the emission of the red light R, as specific light, blue narrow-band light Bn and green light G are sequentially emitted toward the observation target.

In a case where illumination light is emitted using the broadband light source such as a xenon lamp and the rotary filter, in the normal mode, the observation target is imaged using a monochrome image sensor each time the observation target is illuminated with blue light B, green light G, and red light R. The white light image is generated by the B image, the G image, and the R image obtained by imaging the observation target.

In the special mode, the observation target is imaged using a monochrome image sensor during the illumination of white light, that is, each time the observation target is illuminated with blue light B, green light G, and red light R, and the white light image is generated by the B image, the G image, and the R image obtained by such imaging. Further, the observation target is imaged using a monochrome image sensor during the illumination of specific light, that is, each time the observation target is illuminated with the blue narrow-band light Bn and green light G, and the specific light image is generated by the Bn image and the G image obtained by such imaging.

In the embodiment, the invention is applied to the endoscope system that performs processing on the endoscopic image as one of the medical images. However, the invention can also be applied to a medical image processing system that processes medical images other than the endoscopic image. The invention can also be applied to a diagnosis support apparatus for performing diagnosis support for a user using the medical image. The invention can also be applied to a medical service support apparatus for supporting the medical service, such as a diagnostic report, using the medical image.

Figure 22:
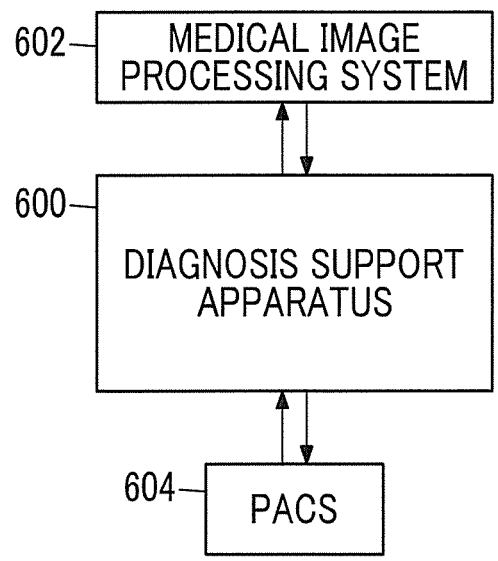
FIG. 22 is a block diagram showing a diagnosis support apparatus.
Figure 23:
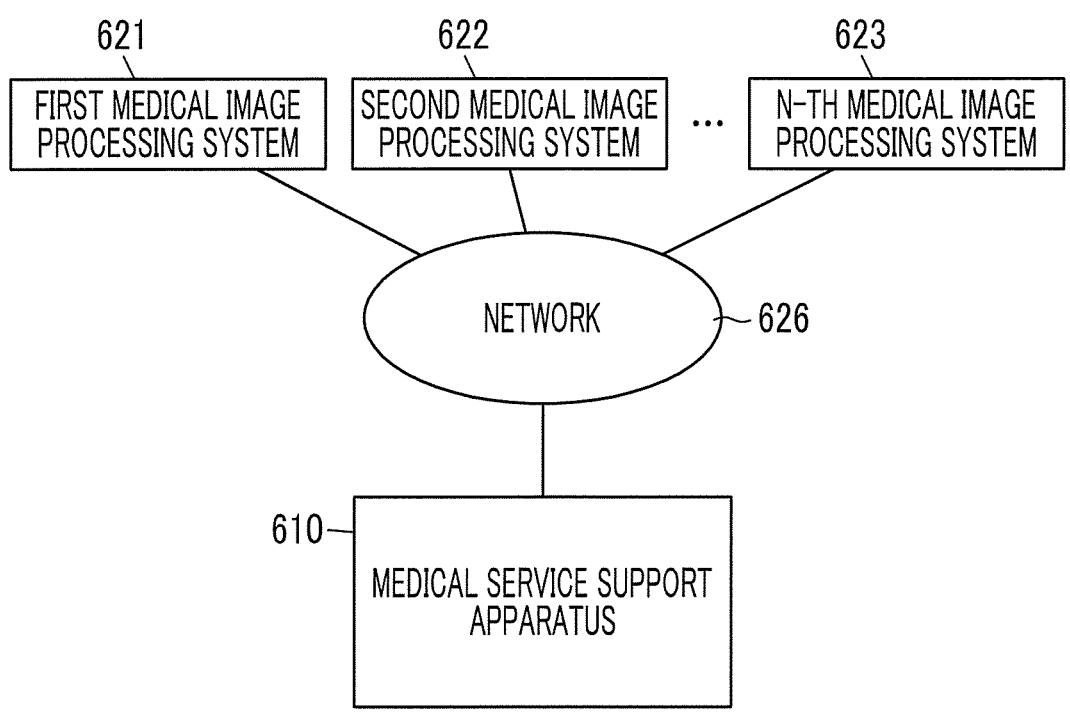
FIG. 23 is a block diagram showing a medical service support apparatus.

For example, as shown in FIG. 22, a diagnosis support apparatus 600 is used in combination with a modality such as a medical image processing system 602 and picture archiving and communication systems (PACS) 604. As shown in FIG. 23, a medical service support apparatus 610 is connected to various inspection devices such as a first medical image processing system 621, a second medical image processing system 622, ..., and an N-th medical image processing system 623 via any network 626. The medical service support apparatus 610 receives medical images from the first to N-th medical image processing systems 621, 622, ..., and 623, and supports the medical service on the basis of the received medical images.

In the embodiment, the hardware structure of the processing units executing various kinds of processing, such as the white light image processing unit 70, the moving speed calculation unit 72, the region-of-interest detection unit 74, the specific light detection result decision unit 76, the discrimination unit 78, and the discrimination result decision unit 80 included in the image processing unit 61 is various processors as follows. The various processors include a central processing unit (CPU) as a general-purpose processor functioning as various processing units by executing software (program), a programmable logic device (PLD) as a processor of which the circuit configuration can be changed after manufacturing such as a field programmable gate array (FPGA), a dedicated electrical circuit as a processor having a circuit configuration designed exclusively for executing various kinds of processing, and a graphical processing unit (GPU), and the like.

One processing unit may be configured by one of the various processors, or configured by a combination of the same or different kinds of two or more processors (for example, combination of a plurality of FPGAs, combination of the CPU and the FPGA, combination of the CPU and the GPU). In addition, a plurality of processing units may be configured by one processor. As an example where a plurality of processing units are configured by one processor, first, there is an aspect where one processor is configured by a combination of one or more CPUs and software as typified by a computer, such as a client or a server, and this processor functions as a plurality of processing units. Second, there is an aspect where a processor fulfilling the functions of the entire system including a plurality of processing units by one integrated circuit (IC) chip as typified by a system on chip (SoC) or the like is used. Thus, various processing units are configured by using one or more of the above-described various processors as hardware structures.

Furthermore, the hardware structures of the various processors are more specifically electrical circuitry in a form in which circuit elements, such as semiconductor elements, are combined.

EXPLANATION OF REFERENCES

10: endoscope system
12: endoscope
12a: insertion part
12b: operation part
12c: bendable portion
12d: distal end portion
12e: angle knob 12f: forceps inlet
13: zoom operation part
13c: mode switching unit
14: light source device
16: processor device
18: monitor
19: user interface
20: light source unit
20a: violet light emitting diode (V-LED)
20b: blue light emitting diode (B-LED)
20c: green light emitting diode (G-LED)
20d: red light emitting diode (R-LED)
21: light emission amount measurement unit
22: light source control unit
23: wavelength cut filter
30a: illumination optical system
30b: imaging optical system
32: illumination lens
41: light guide
45: illumination lens
46: objective lens
47: zoom lens
48: image sensor
49: zoom information output unit
52: central control unit
54: image acquisition unit
56: digital signal processor (DSP)
58: noise reduction unit
59: conversion unit
61: image processing unit
66: display control unit
70: white light image processing unit
72: moving speed calculation unit
74: region-of-interest detection unit
76: specific light detection result decision unit
78: discrimination unit
80: discrimination result decision unit
104: blue laser light source
106: blue-violet laser light source
110: phosphor
202: broadband light source
204: rotary filter
205: control unit
206: filter switching unit
210: normal mode filter
210a: B filter
210b: G filter
210c: R filter
212: special mode filter
212a: B filter
212b: G filter
212c: R filter
212d: Bn filter
212e: Gn filter
600: diagnosis support apparatus
602: medical image processing system
604: PACS
610: medical service support apparatus
621: first medical image processing system
622: second medical image processing system
623: N-th medical image processing system
626: network

What is claimed is:

1. A medical image processing system comprising:
a light source that emits white light or specific light having a spectrum different from a spectrum of the white light;
an image sensor configured to acquire a white light image by imaging an observation target being illuminated with the white light, and acquires a specific light image by imaging the observation target being illuminated with the specific light; and
a processor configured to acquire at least one of a moving speed of the image sensor, zoom information relating to zooming of enlarging the observation target, or a light emission amount of the white light or the specific light;
wherein the processor is configured to control the number of light emission frames of the white light and the number of light emission frames of the specific light in one light emission cycle according to the at least one of the moving speed of the image sensor, the zoom information, or the light emission amount of the white light or the specific light,
wherein the processor is configured to perform control to set a light emission pattern to the light source such that the number of light emission frames of the specific light is greater than the number of light emission frames of the white light at a time of using the zooming, and perform control such that the number of light emission frames of the white light is greater than the number of light emission frames of the specific light at a time of not using the zooming.

2. The medical image processing system according to claim 1,
wherein the processor is configured to perform region-of-interest detection processing for detecting a region of interest from the specific light image; and
a display configured to display a region-of-interest display image obtained by superimposing a detection result of the processor on the white light image, wherein the detection result is the detected region of interest.

3. The medical image processing system according to claim 2,
wherein the processor is configured to, in a case where a plurality of the specific light images are obtained from a plurality of light emission frames of the specific light and the region-of-interest detection processing is performed on the specific light images, decide a specific light detection result to be reflected in the white light image on the basis of a detection result of the region-of-interest detection processing on the specific light images.

4. The medical image processing system according to claim 3,
wherein in a case where both results with the detection of the region of interest and results without the detection of the region of interest are obtained for the same region of the observation target from the plurality of specific light images, the processor is configured to decide, as the specific light detection result, any of the results with the detection of the region of interest or the results without the detection of the region of interest by a majority based on the number of results with the detection of the region of interest and the number of results without the detection of the region of interest.

5. The medical image processing system according to claim 2,
wherein the processor is configured to perform discrimination processing for discriminating the observation target included in the region of interest by displaying a result of the discrimination processing on the display, wherein the result of the discrimination processing is expressed by a stage decided according to a state of the observation target.

6. The medical image processing system according to claim 5,
wherein the processor is configured to, in a case where a plurality of the specific light images are obtained from a plurality of light emission frames of the specific light, the region-of-interest detection processing is performed on the specific light images, and the discrimination processing is performed on the regions of interest detected in the region-of-interest detection processing, decide a specific light discrimination result to be displayed on the display on the basis of a result of the discrimination processing on the regions of interest.

7. The medical image processing system according to claim 6,
wherein the processor is configured to, in a case where a plurality of results of the discrimination processing with different stages are obtained for the same region of interest, decide the stage as the specific light discrimination result by a majority based on the plurality of results of the discrimination processing,
wherein the majority represents that a number of the same region of interest corresponding to results of the discrimination processing of the stage is more than a number of the same region of interest corresponding to results of the discrimination processing of other stages.

8. The medical image processing system according to claim 6,
wherein the processor is configured to, in a case where a plurality of results of the discrimination processing with different stages are obtained for the same region of interest, decide the stage as the specific light discrimination result by averaging the plurality of results of the discrimination processing,
wherein the averaging s the mean of e plurality of results of discrimination processing.

9. The medical image processing system according to claim 5,
wherein in a case where the discrimination processing is performed, the light source emits illumination light for discrimination instead of or in addition to the specific light.

10. The medical image processing system according to claim 9,
wherein 410 nm is included in a peak wavelength of the illumination light for discrimination.

11. The medical image processing system according to claim 1,
wherein 450 nm is included in a peak wavelength of the specific light.

12. A diagnosis support apparatus comprising the medical image processing system according to claim 1.

13. A medical service support apparatus comprising the medical image processing system according to claim 1.

14. A medical image processing system comprising:
a light source that emits white light or specific light having a spectrum different from a spectrum of the white light;
an image sensor configured to acquire a white light image by imaging an observation target being illuminated with the white light, and acquires a specific light image by imaging the observation target being illuminated with the specific light; and
a processor configured to acquire at least one of a moving speed of the image sensor, zoom information relating to zooming of enlarging the observation target, or a light emission amount of the white light or the specific light;
wherein the processor is configured to control the number of light emission frames of the white light and the number of light emission frames of the specific light in one light emission cycle according to the at least one of the moving speed of the image sensor, the zoom information, or the light emission amount of the white light or the specific light,
wherein the processor is configured to perform control to set a light emission pattern to the light source such that the number of light emission frames of the white light is greater than the number of light emission frames of the specific light in one light emission cycle in a case where the moving speed of the imaging unit exceeds a speed threshold, and perform control such that the number of light emission frames of the specific light is greater than the number of light emission frames of the white light in one light emission cycle in a case where the moving speed of the imaging unit is equal to or less than the speed threshold.

15. A medical image processing system comprising:
a light source that emits white light or specific light having a spectrum different from a spectrum of the white light;
an image sensor configured to acquire a white light image by imaging an observation target being illuminated with the white light, and acquires a specific light image by imaging the observation target being illuminated with the specific light; and
a processor configured to acquire at least one of a moving speed of the image sensor, zoom information relating to zooming of enlarging the observation target, or a light emission amount of the white light or the specific light;
wherein the processor is configured to control the number of light emission frames of the white light and the number of light emission frames of the specific light in one light emission cycle according to the at least one of the moving speed of the image sensor, the zoom information, or the light emission amount of the white light or the specific light,
wherein the processor is configured to perform control to set a light emission pattern to the light source such that the number of light emission frames of the white light is greater than the number of light emission frames of the specific light in one light emission cycle in a case where the light emission amount of the white light or the specific light exceeds a light emission amount threshold, and perform control such that the number of light emission frames of the specific light is greater than the number of light emission frames of the white light in one light emission cycle in a case where the light emission amount of the white light or the specific light is equal to or less than the light emission amount threshold.

* * * * *